(12) United States Patent
Kimura et al.

(10) Patent No.: US 7,885,769 B2
(45) Date of Patent: Feb. 8, 2011

(54) SCREENING METHOD AND APPARATUS

(75) Inventors: Toshihito Kimura, Ashigarakami-gun (JP); Hisashi Ohtsuka, Ashigarakami-gun (JP); Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 417 days.

(21) Appl. No.: 11/656,945

(22) Filed: Jan. 24, 2007

(65) Prior Publication Data

US 2007/0172891 A1    Jul. 26, 2007

(30) Foreign Application Priority Data

Jan. 24, 2006    (JP)    ............................. 2006-014599

(51) Int. Cl.
*G01N 33/48*    (2006.01)
(52) U.S. Cl. ...................................... 702/19
(58) Field of Classification Search .................... 702/19
See application file for complete search history.

(56) References Cited

FOREIGN PATENT DOCUMENTS

| JP | 3294605 B2 | 4/2002 |
|---|---|---|
| JP | 2005-189061 A | 7/2005 |
| WO | 90/05295 A1 | 5/1990 |

OTHER PUBLICATIONS

Takayuki Okamoto, "Surface Refracto-sensor using Evanescent Waves: Principles and Instrumentations", Spectrum Research, Dec. 8, 1997, pp. 19-28, vol. 47, No. 1, Optical Engineering Laboratory, The Institute of Physical and Chemical Research (RIKEN), Saitama, Japan.
Kazuhiro Nagata, et al., "Methods of Experiments and Real-Time Analysis of Interaction with Biological Materials", Principe of Biacore, 1998, pp. 27-34, Published by Springer Verlag Tokyo K.K.
Office Action in corresponding Japanese patent application JP 2006-014599, dated Dec. 21, 2010.

*Primary Examiner*—Jerry Lin
(74) *Attorney, Agent, or Firm*—Sughrue Mion, PLLC

(57) ABSTRACT

Reference data are subtracted from corresponding actual measurement data, and unprocessed binding quantity data, each of which represents a quantity of binding of a ligand and each of analytes, are thereby acquired. Calculation is made to find a relationship between the reference data and the unprocessed binding quantity data acquired in cases where the binding does not occur. In accordance with the relationship, variation components, which are contained in the unprocessed binding quantity data, are calculated. The variation components are subtracted from the corresponding unprocessed binding quantity data, and processed binding quantity data are thereby acquired. The processed binding quantity data are utilized for extracting an analyte capable of binding with the ligand.

10 Claims, 7 Drawing Sheets

SCREENING METHOD AND APPARATUS

BACKGROUND OF THE INVENTION

1. Field of the Invention

This invention relates to a screening method and apparatus. This invention particularly relates to a screening method and apparatus for performing a screening operation in accordance with binding quantity data, each of which represents a quantity of binding of a ligand and an analyte with each other and each of which has been obtained with measurement utilizing a refractive index alteration occurring at an interface on a base body block.

2. Description of the Related Art

Ordinarily, the majority of compounds constituting pharmaceutical preparations fulfill their functions by undergoing chemical binding with proteins in living bodies. Therefore, for development of a pharmaceutical preparation, it is important to investigate whether a compound acting as a candidate for the pharmaceutical preparation is or is not capable of undergoing chemical binding with a protein. In particular, it is ideal that a compound constituting a pharmaceutical preparation has the binding ability with respect to only a protein of interest and does not have the binding ability with respect to the other proteins. Specifically, if the compound constituting the pharmaceutical preparation has the binding ability with respect to the proteins other than the protein of interest, the compound will have adverse side effects. In view of the above circumstances, in the field of the development of pharmaceutical preparations, screening operations have heretofore been performed for extracting a compound, which has the binding ability with respect to only a protein of interest, from compounds acting as the candidates for the pharmaceutical preparations.

Various types of apparatuses have heretofore been proposed for the screening operations performed on the compounds acting as the candidates for the pharmaceutical preparations. For example, there has been known an analysis apparatus for causing a surface plasmon to occur through total reflection of a light beam from a metal surface, and for making an analysis by the utilization of an alteration of a specific reflection angle, i.e. an attenuated total reflection angle (an ATR angle), which is associated with the occurrence of marked attenuation of an optical intensity (i.e., attenuated total reflection) in the light beam having been totally reflected from the metal surface, and which alters in accordance with a dielectric constant (or a refractive index) in the vicinity of the metal surface. (The aforesaid analysis apparatus is described in, for example, "Surface Refracto-sensor using Evanescent Waves: Principles and Instrumentations" by T. Okamoto, Spectrum Research, Vol. 47, No. 1, pp. 19-28, 1997.) Also, as an apparatus utilizing the principle of the surface plasmon described above, there has heretofore been known, for example, BIACORE 3000 supplied by Biacore K.K. (The apparatus utilizing the principle of the surface plasmon is described in, for example, "Methods of Experiments and Real-Time Analysis of Interaction with Biological Materials" by Kazuhiro Nagata & Hiroshi Handa, Published by Springer Verlag Tokyo K.K., pp. 27-34, 1998)

By use of the apparatuses of the types described above, studies have heretofore been made on techniques for obtaining measurement data, which represent binding quantities between a single kind of a protein and multiple kinds, e.g., 10,000 kinds, of compounds, and for extracting hit compounds, which are the compounds capable of undergoing the binding with the single kind of the protein, from the multiple kinds of the compounds and in accordance with the measurement data.

Ordinarily, the hit compounds, which are extracted with the compound screening operation as described above, are approximately 1% of the multiple kinds of the compounds subjected to the screening operation. Specifically, ordinarily, approximately 100 kinds of compounds are extracted as the hit compounds from 10,000 kinds of compounds subjected to the screening operation. Also, two to three days or more days are often required for the screening operation performed on the multiple kinds of the compounds.

As for the aforesaid analysis utilizing the attenuated total reflection, there has heretofore been known a technique, wherein an identical compound solution is retained on an actual measurement region, in which a protein has been fixed on a gold film having been formed on a surface of a transparent dielectric material block, and on a reference measurement region, in which the protein has not been fixed on the gold film, and wherein the quantity of binding of the compound, which is contained in the compound solution, and the protein with each other is measured. The quantity of the binding of the compound, which is contained in the compound solution, and the protein with each other is capable of being calculated from the difference between the ATR angle, which is measured when the compound solution is retained in the actual measurement region, and the ATR angle, which is measured when the compound solution is retained in the reference measurement region.

In cases where the protein and the compound are not capable of undergoing the binding with each other, the value of the measurement data representing the ATR angle, which is measured when the compound solution is retained in the actual measurement region, and the value of the reference measurement data representing the ATR angle, which is measured when the compound solution is retained in the reference measurement region, will coincide with each other, and the difference between the value of the measurement data and the value of the reference measurement data will be equal to 0. However, for reasons of the measuring system, or the like, it may often occur that the difference between the value of the measurement data and the value of the reference measurement data does not become equal to 0. For example, at the time of the measurement made in cases where the protein and the compound are not capable of undergoing the binding with each other, it may often occur that the difference between the ATR angle, which is measured when the compound solution is retained in the actual measurement region, and the ATR angle, which is measured when the compound solution is retained in the reference measurement region, alters in accordance with the magnitude of the refractive index of the compound solution to be analyzed.

Also, there has heretofore been studied a technique for correcting the difference between the ATR angle, which is measured when the compound solution is retained in the actual measurement region, and the ATR angle, which is measured when the compound solution is retained in the reference measurement region and which should fundamentally coincide with the aforesaid ATR angle measured in the actual measurement region. By way of example, the correction technique described below has heretofore been studied. Specifically, with the studied correction technique, multiple kinds of reference liquids having different refractive indexes are prepared. Also, with respect to each of the reference liquids, the difference between the ATR angle measured in the actual measurement region and the ATR angle measured in the reference measurement region is calculated. In this manner, the relationship between the refractive indexes of the reference liquids and the ATR angle differences having been found from the measurements is acquired. Further, the difference between the ATR angle measured in the actual measurement region and the ATR angle measured in the reference measurement region, which difference has been found from the measurements using the compound solution to be analyzed, is corrected in accordance with the relationship between the refractive indexes and the ATR angle differences, which relationship has been acquired by use of the reference liquids.

With the correction technique described above, reference is made to the relationship between the refractive indexes and the ATR angle differences, which relationship has been acquired by use of the reference liquids, and a variation of the difference between the ATR angle measured in the actual measurement region and the ATR angle measured in the reference measurement region, which difference arises in the measurements using the compound solution to be analyzed, is thereby presumed. In accordance with the presumed variation of the difference between the ATR angles, the variation of the difference between the ATR angle measured in the actual measurement region and the ATR angle measured in the reference measurement region is capable of being corrected.

However, the problems described below are encountered with the correction technique described above. Specifically, at the time at which the relationship between the refractive indexes and the ATR angle differences is acquired by use of the reference liquids, a variation of the environmental temperature, a variation of the concentrations (a variation of the refractive indexes) of the reference liquids due to evaporation, and the like, occur. Therefore, it is not always possible to acquire the accurate relationship between the refractive indexes and the ATR angle differences. Also, in cases where it is intended to obtain a large quantity of measurement data such that the relationship between the refractive indexes and the ATR angle differences may be acquired accurately, the measurements for the compound solutions to be subjected to the screening operation are not capable of being performed promptly, and the operation efficiency of the screening apparatus is not capable of being kept high. Therefore, there is a strong demand for a technique, with which the variation of the difference between the ATR angle measured in the actual measurement region and the ATR angle measured in the reference measurement region is capable of being corrected more accurately, and with which the reliability of the screening operation is capable of being enhanced, such that the efficiency of the screening operation may not become low.

The problems described above are encountered in cases where the screening operation is performed in accordance with the quantity of the binding of the ligand and the analyte with each other, which quantity of the binding has been obtained with measurements utilizing the ATR angle. The problems described above are also encountered in cases where the screening operation is performed in accordance with the quantity of the binding of the ligand and the analyte with each other, which quantity of the binding has been obtained with measurements utilizing the refractive index alteration occurring at the interface on the base body block.

SUMMARY OF THE INVENTION

The primary object of the present invention is to provide a screening method, with which reliability of a screening operation is capable of being enhanced, such that an efficiency of the screening operation may not become low.

Another object of the present invention is to provide an apparatus for carrying out the screening method.

The present invention provides a first screening method, in which binding quantity data each representing a quantity of binding of a single kind of a ligand and each of multiple kinds of analytes with each other are acquired from measurement of a refractive index alteration quantity at an interface of an actual measurement region or a reference measurement region on a base body block, and in which an analyte capable of undergoing the binding with the ligand is extracted from the multiple kinds of the analytes and in accordance with the binding quantity data, the method comprising the steps of:

i) performing operations for bringing each of analyte solutions, each of which contains one of the multiple kinds of the analytes, successively into contact with the actual measurement region, to which the single kind of the ligand has been fixed, ii) acquiring values of actual measurement data, each of which represents the refractive index alteration quantity, from the operations for bringing each of the analyte solutions successively into contact with the actual measurement region, iii) performing operations for bringing each of the analyte solutions into contact with the reference measurement region, iv) acquiring values of reference measurement data, each of which represents the refractive index alteration quantity and corresponds to one of the actual measurement data, from the operations for bringing each of the analyte solutions into contact with the reference measurement region, v) subtracting each of the values of the reference measurement data from the corresponding one of the values of the actual measurement data, unprocessed binding quantity data being thereby acquired, vi) calculating a relationship between the values of the reference measurement data and the values of the unprocessed binding quantity data, which vary in accordance with the values of the reference measurement data, the values of the reference measurement data and the values of the unprocessed binding quantity data having been acquired in cases where each of the analytes and the single kind of the ligand have not undergone the binding with each other, vii) making calculation in accordance with the thus calculated relationship to find each of variation components, each of which is contained in one of the unprocessed binding quantity data and corresponds to one of the reference measurement data having been acquired in cases where each of the analytes and the single kind of the ligand have not undergone the binding with each other and in cases where each of the analytes and the single kind of the ligand have undergone the binding with each other, viii) subtracting each of the values of the variation components, each of which is contained in one of the unprocessed binding quantity data, from the corresponding one of the values of the unprocessed binding quantity data, processed binding quantity data being thereby acquired, and ix) utilizing the thus acquired processed binding quantity data as the binding quantity data for use in extracting the analyte, which is capable of undergoing the binding with the ligand.

The present invention also provides a second screening method, in which binding quantity data each representing a quantity of binding of a single kind of an analyte and each of multiple kinds of ligands with each other are acquired from measurement of a refractive index alteration quantity at an interface of each of actual measurement regions or each of reference measurement regions on a base body block, and in which a ligand capable of undergoing the binding with the analyte is extracted from the multiple kinds of the ligands and in accordance with the binding quantity data, the method comprising the steps of:

i) performing operations for bringing an analyte solution, which contains the single kind of the analyte, successively into contact with each of the actual measurement regions, each of the multiple kinds of the ligands having been fixed to one of the actual measurement regions, ii) acquiring values of actual measurement data, each of which represents the refractive index alteration quantity, from the operations for bringing the analyte solution successively into contact with each of the actual measurement regions, iii) performing operations for bringing the analyte solution into contact with each of the reference measurement regions, iv) acquiring values of reference measurement data, each of which represents the refractive index alteration quantity and corresponds to one of the actual measurement data, from the operations for bringing the analyte solution into contact with each of the reference measurement regions, v) subtracting each of the values of the reference measurement data from the corresponding one of the values of the actual measurement data, unprocessed binding quantity data being thereby acquired, vi) calculating a relationship between the values of the reference measurement data and the values of the unprocessed binding quantity data, which vary in accordance with the values of the reference measurement data, the values of the reference measurement data and the values of the unprocessed binding quantity data having been acquired in cases where the analyte and each of the ligands have not undergone the binding with each other, vii) making calculation in accordance with the thus calculated relationship to find each of variation components, each of which is contained in one of the unprocessed binding quantity data and corresponds to one of the reference measurement data having been acquired in cases where the analyte and each of the ligands have not undergone the binding with each other and in cases where the analyte and each of the ligands have undergone the binding with each other, viii) subtracting each of the values of the variation components, each of which is contained in one of the unprocessed binding quantity data, from the corresponding one of the values of the unprocessed binding quantity data, processed binding quantity data being thereby acquired, and ix) utilizing the thus acquired processed binding quantity data as the binding quantity data for use in extracting the ligand, which is capable of undergoing the binding with the analyte.

Each of the first and second screening methods in accordance with the present invention may be modified such that the variation components are calculated with a function which approximately represents the relationship between the values of the reference measurement data and the values of the unprocessed binding quantity data. In such cases, the function may be a linear function, a quadratic function, or a cubic function.

Also, each of the first and second screening methods in accordance with the present invention may be modified such that the refractive index alteration quantity occurs due to surface plasmon resonance.

The term "ligand" as used herein means the substance, which has been fixed to the base body block and is capable of undergoing specific binding with a specific substance.

The term "analyte" as used herein means the substance to be analyzed, which is subjected to the binding with the ligand.

The term "actual measurement region" as used herein means the region on the base body block, to which region the ligand has been fixed.

The term "reference measurement region" as used herein means the region on the base body block, to which region the ligand has not been fixed, and to which region only a base layer for the ligand fixation has been fixed. The base layer may be constituted of a metal film, or the like.

The base body block may be constituted of a dielectric material block. For example, the base body block may be constituted of a transparent prism made from glass, an acrylic resin, or the like.

The first screening method in accordance with the present invention may be constituted as a screening method, in which binding quantity data each representing a quantity of binding of a single kind of a ligand and each of multiple kinds of analytes with each other are acquired from measurement utilizing attenuated total reflection, and in which an analyte capable of undergoing the binding with the ligand is extracted from the multiple kinds of the analytes and in accordance with the binding quantity data, the method comprising the steps of:

i) performing operations for bringing each of analyte solutions, each of which contains one of the multiple kinds of the analytes, successively into contact with an actual measurement region on a dielectric material block, to which actual measurement region the single kind of the ligand has been fixed, ii) acquiring values of actual measurement data, each of which represents an attenuated total reflection angle, from the operations for bringing each of the analyte solutions successively into contact with the actual measurement region, iii) performing operations for bringing each of the analyte solutions into contact with a reference measurement region on the dielectric material block, iv) acquiring values of reference measurement data, each of which represents the attenuated total reflection angle and corresponds to one of the actual measurement data, from the operations for bringing each of the analyte solutions into contact with the reference measurement region, v) subtracting each of the values of the reference measurement data from the corresponding one of the values of the actual measurement data, unprocessed binding quantity data being thereby acquired, vi) calculating a relationship between the values of the reference measurement data and the values of the unprocessed binding quantity data, which vary in accordance with the values of the reference measurement data, the values of the reference measurement data and the values of the unprocessed binding quantity data having been acquired in cases where each of the analytes and the single kind of the ligand have not undergone the binding with each other, vii) making calculation in accordance with the thus calculated relationship to find each of variation components, each of which is contained in one of the unprocessed binding quantity data and corresponds to one of the reference measurement data having been acquired in cases where each of the analytes and the single kind of the ligand have not undergone the binding with each other and in cases where each of the analytes and the single kind of the ligand have undergone the binding with each other, viii) subtracting each of the values of the variation components, each of which is contained in one of the unprocessed binding quantity data, from the corresponding one of the values of the unprocessed binding quantity data, processed binding quantity data being thereby acquired, and ix) utilizing the thus acquired processed binding quantity data as the binding quantity data for use in extracting the analyte, which is capable of undergoing the binding with the ligand.

The second screening method in accordance with the present invention may be constituted as a screening method, in which binding quantity data each representing a quantity of binding of a single kind of an analyte and each of multiple kinds of ligands with each other are acquired from measurement utilizing attenuated total reflection, and in which a ligand capable of undergoing the binding with the analyte is extracted from the multiple kinds of the ligands and in accordance with the binding quantity data, the method comprising the steps of:

i) performing operations for bringing an analyte solution, which contains the single kind of the analyte, successively into contact with each of actual measurement regions on a dielectric material block, each of the multiple kinds of the ligands having been fixed to one of the actual measurement regions, ii) acquiring values of actual measurement data, each of which represents an attenuated total reflection angle, from the operations for bringing the analyte solution successively into contact with each of the actual measurement regions, iii) performing operations for bringing the analyte solution into contact with each of reference measurement regions on the dielectric material block, iv) acquiring values of reference measurement data, each of which represents the attenuated total reflection angle and corresponds to one of the actual measurement data, from the operations for bringing the analyte solution into contact with each of the reference measurement regions, v) subtracting each of the values of the reference measurement data from the corresponding one of the values of the actual measurement data, unprocessed binding quantity data being thereby acquired, vi) calculating a relationship between the values of the reference measurement data and the values of the unprocessed binding quantity data, which vary in accordance with the values of the reference measurement data, the values of the reference measurement data and the values of the unprocessed binding quantity data having been acquired in cases where the analyte and each of the ligands have not undergone the binding with each other, vii) making calculation in accordance with the thus calculated relationship to find each of variation components, each of which is contained in one of the unprocessed binding quantity data and corresponds to one of the reference measurement data having been acquired in cases where the analyte and each of the ligands have not undergone the binding with each other and in cases where the analyte and each of the ligands have undergone the binding with each other, viii) subtracting each of the values of the variation components, each of which is contained in one of the unprocessed binding quantity data, from the corresponding one of the values of the unprocessed binding quantity data, processed binding quantity data being thereby acquired, and ix) utilizing the thus acquired processed binding quantity data as the binding quantity data for use in extracting the ligand, which is capable of undergoing the binding with the analyte.

The present invention further provides a first screening apparatus, comprising:

i) an analysis section for acquiring binding quantity data, each of which represents a quantity of binding of a single kind of a ligand and each of multiple kinds of analytes with each other, from measurement of a refractive index alteration quantity at an interface of an actual measurement region or a reference measurement region on a base body block, and ii) a screening section for extracting an analyte, which is capable of undergoing the binding with the ligand, from the multiple kinds of the analytes and in accordance with the binding quantity data, the analysis section being constituted for:

a) performing operations for bringing each of analyte solutions, each of which contains one of the multiple kinds of the analytes, successively into contact with the actual measurement region, to which the single kind of the ligand has been fixed, b) acquiring values of actual measurement data, each of which represents the refractive index alteration quantity, from the operations for bringing each of the analyte solutions successively into contact with the actual measurement region, c) performing operations for bringing each of the analyte solutions into contact with the reference measurement region, and d) acquiring values of reference measurement data, each of which represents the refractive index alteration quantity and corresponds to one of the actual measurement data, from the operations for bringing each of the analyte solutions into contact with the reference measurement region, and the screening section being provided with:

a) a storage section for storing information representing the values of the actual measurement data and the values of the reference measurement data, which have been acquired by the analysis section, b) a pre-processing section for subtracting each of the values of the reference measurement data from the corresponding one of the values of the actual measurement data, and thereby acquiring unprocessed binding quantity data, c) a variation relationship acquiring section for calculating a relationship between the values of the reference measurement data and the values of the unprocessed binding quantity data, which vary in accordance with the values of the reference measurement data, the values of the reference measurement data and the values of the unprocessed binding quantity data having been acquired in cases where each of the analytes and the single kind of the ligand have not undergone the binding with each other, d) a variation component acquiring section for making calculation in accordance with the thus calculated relationship to find each of variation components, each of which is contained in one of the unprocessed binding quantity data and corresponds to one of the reference measurement data having been acquired in cases where each of the analytes and the single kind of the ligand have not undergone the binding with each other and in cases where each of the analytes and the single kind of the ligand have undergone the binding with each other, and e) a processed binding quantity acquiring section for subtracting each of the values of the variation components, each of which is contained in one of the unprocessed binding quantity data, from the corresponding one of the values of the unprocessed binding quantity data, and thereby acquiring processed binding quantity data, the thus acquired processed binding quantity data being utilized as the binding quantity data for use in extracting the analyte, which is capable of undergoing the binding with the ligand.

The present invention still further provides a second screening apparatus, comprising:

i) an analysis section for acquiring binding quantity data, each of which represents a quantity of binding of a single kind of an analyte and each of multiple kinds of ligands with each other, from measurement of a refractive index alteration quantity at an interface of each of actual measurement regions or each of reference measurement regions on a base body block, and ii) a screening section for extracting a ligand, which is capable of undergoing the binding with the analyte, from the multiple kinds of the ligands and in accordance with the binding quantity data, the analysis section being constituted for:

a) performing operations for bringing an analyte solution, which contains the single kind of the analyte, successively into contact with each of the actual measurement regions, each of the multiple kinds of the ligands having been fixed to one of the actual measurement regions, b) acquiring values of actual measurement data, each of which represents the refractive index alteration quantity, from the operations for bringing the analyte solution successively into contact with each of the actual measurement regions, c) performing operations for bringing the analyte solution into contact with each of the reference measurement regions, and d) acquiring values of reference measurement data, each of which represents the refractive index alteration quantity and corresponds to one of the actual measurement data, from the operations for bringing the analyte solution into contact with each of the reference measurement regions, and the screening section being provided with:

a) a storage section for storing information representing the values of the actual measurement data and the values of the reference measurement data, which have been acquired by the analysis section, b) a pre-processing section for subtracting each of the values of the reference measurement data from the corresponding one of the values of the actual measurement data, and thereby acquiring unprocessed binding quantity data, c) a variation relationship acquiring section for calculating a relationship between the values of the reference measurement data and the values of the unprocessed binding quantity data, which vary in accordance with the values of the reference measurement data, the values of the reference measurement data and the values of the unprocessed binding quantity data having been acquired in cases where the analyte and each of the ligands have not undergone the binding with each other, d) a variation component acquiring section for making calculation in accordance with the thus calculated relationship to find each of variation components, each of which is contained in one of the unprocessed binding quantity data and corresponds to one of the reference measurement data having been acquired in cases where the analyte and each of the ligands have not undergone the binding with each other and in cases where the analyte and each of the ligands have undergone the binding with each other, and e) a processed binding quantity acquiring section for subtracting each of the values of the variation components, each of which is contained in one of the unprocessed binding quantity data, from the corresponding one of the values of the unprocessed binding quantity data, and thereby acquiring processed binding quantity data, the thus acquired processed binding quantity data being utilized as the binding quantity data for use in extracting the ligand, which is capable of undergoing the binding with the analyte.

Each of the first screening method and apparatus in accordance with the present invention and the second screening method and apparatus in accordance with the present invention is based upon the findings that the majority of the combinations of the ligands and the analytes, which are to be subjected to the screening operation, are the combinations of the ligands and the analytes, which are not capable of undergoing the binding with each other, and that the values of the actual measurement data and the values of the reference measurement data, each of which represents the refractive index alteration quantity acquired in cases where the analyte and the ligand are not capable of undergoing the binding with each other, should fundamentally coincide with each other regardless of the kinds of the combinations.

With each of the first screening method and apparatus in accordance with the present invention and the second screening method and apparatus in accordance with the present invention, the calculation is made to find the relationship between the values of the reference measurement data and the values of the unprocessed binding quantity data, which vary in accordance with the values of the reference measurement data, the values of the reference measurement data and the values of the unprocessed binding quantity data having been acquired in cases where the analyte and the ligand have not undergone the binding with each other. Also, in accordance with the thus calculated relationship, the calculation is made to find each of variation components, each of which is contained in one of the unprocessed binding quantity data and corresponds to one of the reference measurement data having been acquired in cases where the analyte and the ligand have not undergone the binding with each other and in cases where the analyte and the ligand have undergone the binding with each other. Further, each of the values of the variation components, each of which is contained in one of the unprocessed binding quantity data, is subtracted from the corresponding one of the values of the unprocessed binding quantity data, the processed binding quantity data being thereby acquired. The thus acquired processed binding quantity data are utilized as the binding quantity data for use in extracting the analyte, which is capable of undergoing the binding with the ligand, or the ligand, which is capable of undergoing the binding with the analyte. Therefore, the reliability of the screening operation is capable of being enhanced, such that the efficiency of the screening operation may not become low.

Specifically, as the data for use in calculating the relationship described above, it is possible to utilize the data having been obtained from the measurement of the refractive index alteration quantity (or the measurement of the ATR angle) having been made with respect to the ligand and the analyte to be subjected to the screening operation. For example, it is not necessary for particular measurement to be made with respect to the reference liquid, which is not the object of the screening operation, for the calculation of the aforesaid relationship as in the conventional techniques. Therefore, with each of the first screening method and apparatus in accordance with the present invention and the second screening method and apparatus in accordance with the present invention, the efficiency of the screening operation does not become low.

Also, ordinarily, the majority of the combinations of the ligands and the analytes, which are to be subjected to the screening operation, are the combinations of the ligands and the analytes, which are not capable of undergoing the binding with each other. For example, in cases where 99% of the combinations of the ligands and the analytes, which are to be subjected to the screening operation, are the combinations of the ligands and the analytes, which are not capable of undergoing the binding with each other, the majority of the data, each of which has been obtained from the measurement of the refractive index alteration quantity (or the measurement of the ATR angle) having been made with respect to the ligand and the analyte to be subjected to the screening operation, are capable of being utilized as the data for use in calculating the relationship described above. Therefore, as the data for use in calculating the relationship described above, it is possible to utilize a larger quantity of data than, for example, the cases wherein the particular measurement is made with respect to the reference liquid, which is not the object of the screening operation, for the calculation of the aforesaid relationship as in the conventional techniques. Accordingly, the aforesaid relationship is capable of being calculated more accurately. As a result, the reliability of the screening operation is capable of being enhanced.

With each of the first screening method and apparatus in accordance with the present invention and the second screening method and apparatus in accordance with the present invention, wherein the variation components are calculated with the function which approximately represents the relationship between the values of the reference measurement data and the values of the unprocessed binding quantity data, each of the variation components, each of which is contained in one of the unprocessed binding quantity data, is capable of being calculated efficiently. Therefore, the efficiency of the screening operation is capable of being enhanced.

DESCRIPTION OF THE PREFERRED EMBODIMENTS

The present invention will hereinbelow be described in further detail with reference to the accompanying drawings.

Figure 1:
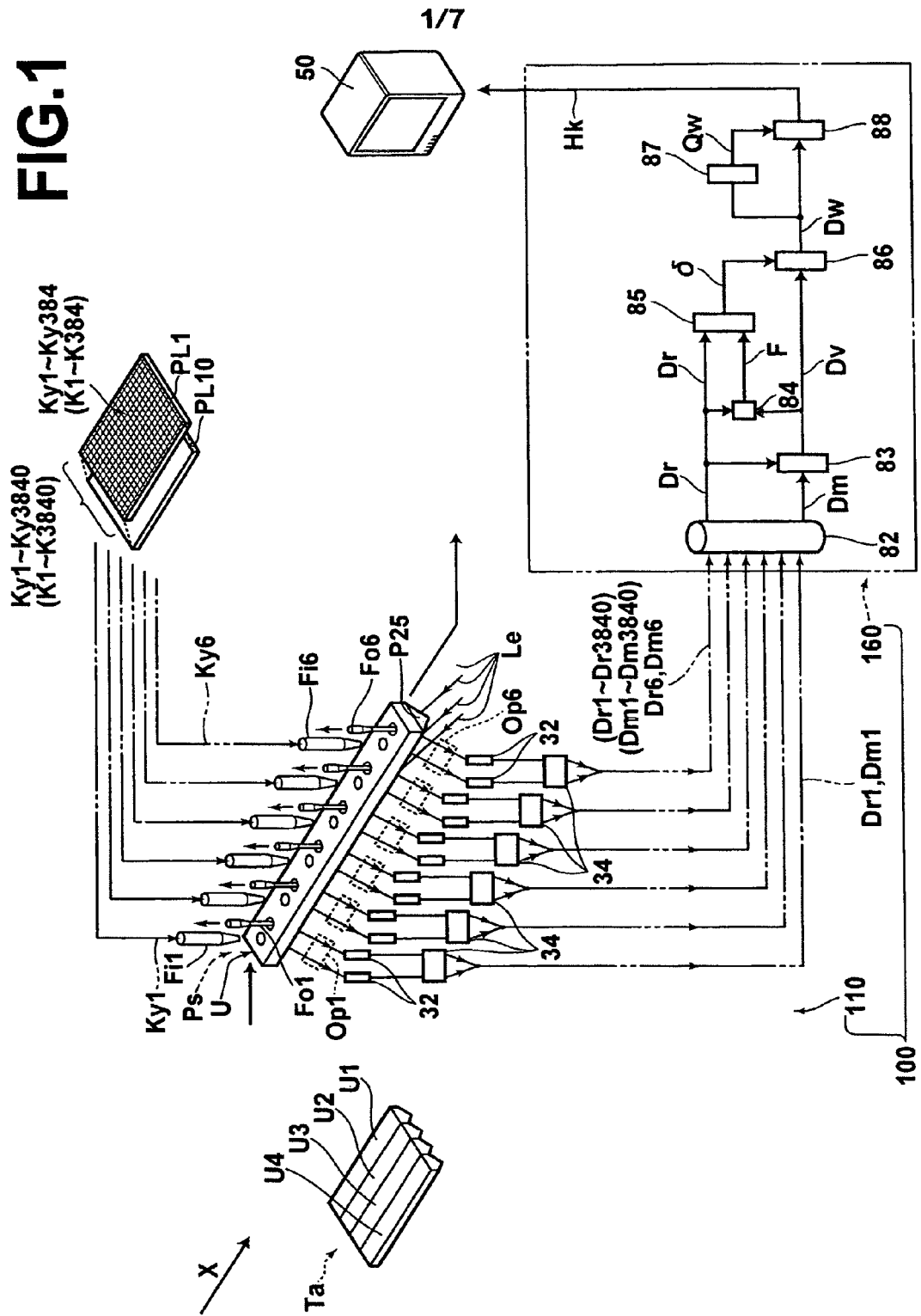
FIG. 1 is a conceptual view showing an embodiment of the screening apparatus for carrying out an embodiment of the screening method in accordance with the present invention.
Figure 2:
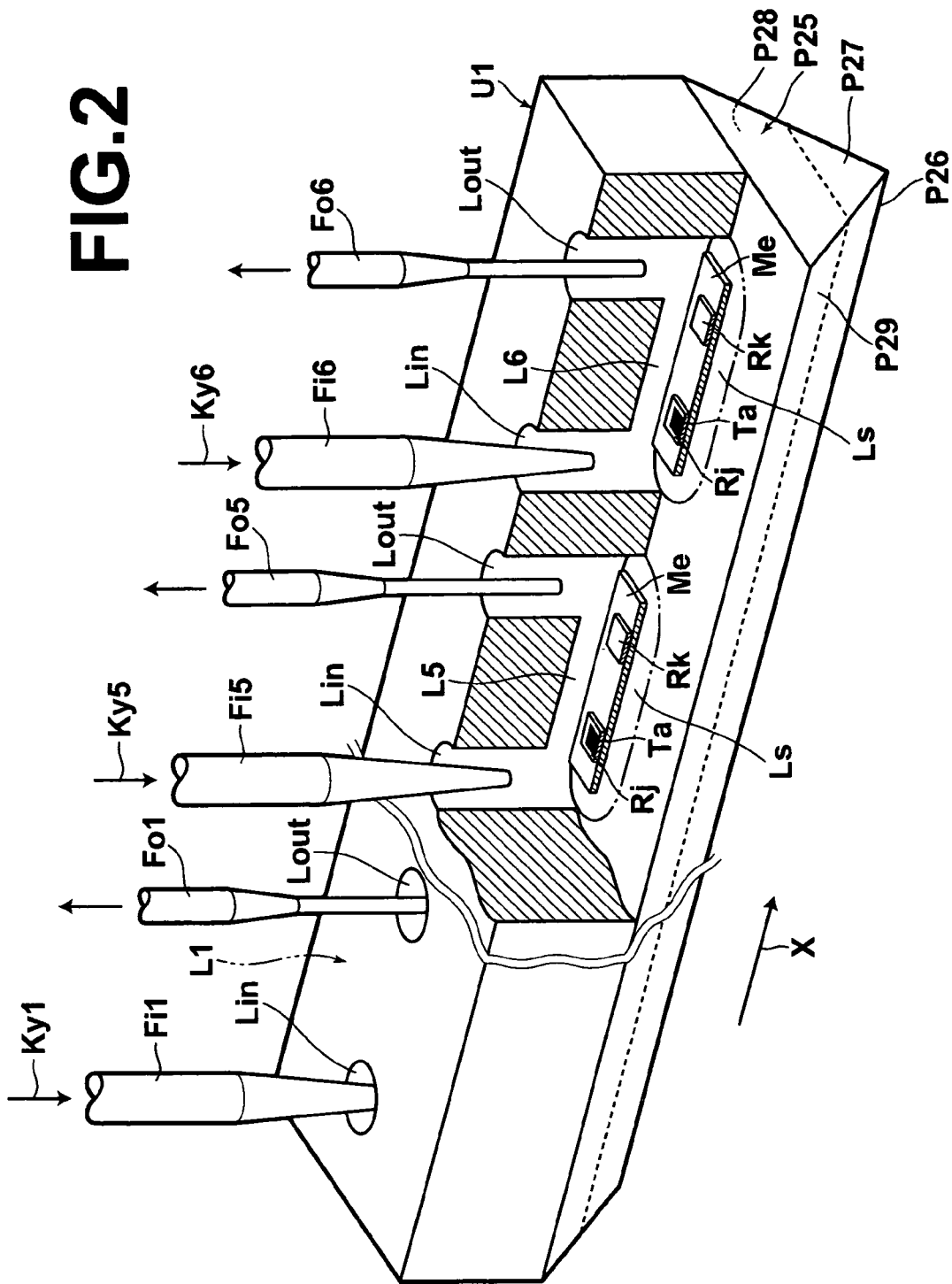
FIG. 2 is an enlarged perspective view showing an analysis vessel.

FIG. 1 is a conceptual view showing an embodiment of the screening apparatus for carrying out an embodiment of the screening method in accordance with the present invention. FIG. 2 is an enlarged perspective view showing an analysis vessel.

With reference to FIG. 1, a screening apparatus 100 for carrying out the embodiment of the screening method in accordance with the present invention comprises an analysis unit 110 and a screening unit 160. The analysis unit 110 performs the measurement of the quantity of the binding of a single kind of a protein Ta and each of multiple kinds of compounds K1, K2, . . . with each other. The screening unit 160 extracts a hit compound Hk, which is capable of undergoing the binding with the protein Ta, from the multiple kinds of the compounds K1, K2, . . . and in accordance with actual measurement data and reference measurement data, which will be described later and which have been acquired from the measurement performed by the analysis unit 110.

The screening unit 160 is provided with a storage section 82 for storing actual measurement data Dm1, Dm2, . . . and reference measurement data Dr1, Dr2, . . . , which have been acquired by the analysis unit 110. The screening unit 160 is also provided with a pre-processing section 83 for subtracting each of the values of the reference measurement data Dr1, Dr2, . . . from the corresponding one of the values of the actual measurement data Dm1, Dm2, . . . , and thereby acquiring unprocessed binding quantity data Dv1, Dv2, . . . . The screening unit 160 is further provided with a variation relationship acquiring section 84 for calculating the relationship between the values of the reference measurement data and the values of the unprocessed binding quantity data, which vary in accordance with the values of the reference measurement data, the values of the reference measurement data and the values of the unprocessed binding quantity data having been acquired in cases where each of the compounds and the single kind of the protein have not undergone the binding with each other. (The relationship between the values of the reference measurement data and the values of the unprocessed binding quantity data, which have been acquired in cases where each of the compounds and the single kind of the protein have not undergone the binding with each other, will hereinbelow be referred to as the variation relationship.)

The actual measurement data Dm1, Dm2, . . . will hereinbelow be collectively referred to also as the actual measurement data Dm. Also, the reference measurement data Dr1, Dr2, . . . will hereinbelow be collectively referred to also as the reference measurement data Dr. Further, the unprocessed binding quantity data Dv1, Dv2, . . . will hereinbelow be collectively referred to also as the unprocessed binding quantity data Dv.

The screening unit 160 is still further provided with a variation component acquiring section 85 for making calculation in accordance with the aforesaid variation relationship to find each of variation components $\delta 1$, $\delta 2$, . . . , each of which is contained in one of the unprocessed binding quantity data Dv1, Dv2, . . . and corresponds to one of the reference measurement data Dr1, Dr2, . . . having been acquired in cases where each of the compounds and the single kind of the protein have not undergone the binding with each other and in cases where each of the compounds and the single kind of the protein have undergone the binding with each other. The screening unit 160 is also provided with a processed binding quantity acquiring section 86 for subtracting each of the values of the variation components $\delta 1$, $\delta 2$, . . . , each of which is contained in one of the unprocessed binding quantity data Dv1, Dv2, . . . , from the corresponding one of the values of the unprocessed binding quantity data Dv1, Dv2, . . . , and thereby acquiring processed binding quantity data Dw1, Dw2, . . . . The thus acquired processed binding quantity data Dw1, Dw2, . . . are utilized as the binding quantity data for use in extracting the compound, which is capable of undergoing the binding with the protein Ta.

The screening unit 160 is further provided with a threshold value setting section 87 for setting a threshold value Qw, which is to be used for the extraction of the hit compound Hk, by use of the processed binding quantity data Dw1, Dw2, . . . having been acquired by the processed binding quantity acquiring section 86. The screening unit 160 is still further provided with a hit compound extracting section 88 for making a comparison between each of the values of the processed binding quantity data Dw1, Dw2, . . . and the threshold value Qw having been set by the threshold value setting section 87, and extracting the hit compound Hk in accordance with the results of the comparison. In this embodiment, the threshold value Qw, which is set by the threshold value setting section 87, is calculated in accordance with a standard deviation of the values of the processed binding quantity data Dw1, Dw2, . . . .

The variation components δ1, δ2, . . . will hereinbelow be collectively referred to also as the variation component δ. Also, the processed binding quantity data Dw1, Dw2, . . . will hereinbelow be collectively referred to also as the processed binding quantity data Dw.

How the screening method is carried out by the screening apparatus 100 will hereinbelow be described in detail.

As illustrated in FIG. 1, the analysis unit 110 performs a day's measurement by use of four analysis vessels U1, U2, U3, and U4 and plates PL1 to PL10. The single kind of the protein Ta, which acts as the ligand, has been fixed to each of the analysis vessels U1, U2, U3, and U4. Each of the plates PL1 to PL10 accommodates compound solutions Ky1, Ky2, . . . . Each of the compound solutions Ky1, Ky2, . . . contains one of different kinds of the compounds K1, K2, . . . , which act as the analytes, in a buffer solution. The analysis vessels U1, U2, U3, and U4 will herein below be collectively referred to also as the analysis vessel U. Also, the multiple kinds of the compounds K1, K2, . . . will hereinbelow be collectively referred to also as the compound K.

Each of the analysis vessels U1, U2, U3, and U4 is used 160 times and is then scrapped.

Each of the plates PL1 to PL10 accommodates 384 kinds of different compound solutions Ky1, Ky2, . . . , which act as the analyte solutions. Therefore, the plates PL1 to PL10 accommodate a total of 3,840 kinds of the compound solutions Ky1 to Ky3840.

By use of the analysis vessels U1, U2, U3, and U4, the analysis unit 110 performs the measurement with respect to the 3,840 kinds of the compound solutions Ky1 to Ky3840, which have been accommodated in the plates PL1 to PL10, in a day.

FIG. 2 is an enlarged perspective view showing the analysis vessel U1. As illustrated in FIG. 2, the analysis vessel U1 (i.e., each analysis vessel U) has a slender shape extending in one direction (i.e., the direction indicated by the arrow X in FIG. 2). The analysis vessel U1 is provided with six measurement flow paths L1 to L6, each of which is formed along the longitudinal direction of the analysis vessel U1 (i.e., along the direction indicated by the arrow X in FIG. 2). The measurement flow paths L1 to L6 have identical shapes. Each of the compound solutions Ky1, Ky2, . . . is caused to flow through one of the measurement flow paths L1 to L6. The measurement flow paths L1 to L6 will hereinbelow be collectively referred to also as the measurement flow path L. The compound solution Ky described above flows through the measurement flow path L in the direction indicated by the arrow X in FIG. 2. A gold film Me has been formed with a sputtering technique on a total reflection surface Ls, which is the bottom surface of each of the six measurement flow paths L1 to L6 in the analysis vessel U1. A slender prism P25, which acts as a base body block, constitutes a part of the analysis vessel U1 and is formed such that the triangular shape extends in the direction indicated by the arrow X in FIG. 2. The total reflection surface Ls described above constitutes one of the prism surfaces of the prism P25 acting as the base body block. The prism 25 is constituted of a dielectric material. The total reflection surface Ls of the prism P25 acting as the dielectric material block is the surface for total reflection of a laser beam Le, which will be described later. In this embodiment, the prism P25 is provided with a triangular prism region P27, which contains an edge line P26 opposite to the total reflection surface Ls described above and which extends in the direction indicated by the arrow X in FIG. 2. Alternatively, the triangular prism region P27 may be removed from the prism P25.

Also, linker films Rj and Rk, which are of an identical kind, are located on the gold film Me, which has been formed on the total reflection surface Ls of each measurement flow path L. Specifically, the linker film Rj is located on the upstream side of the measurement flow path L, and the linker film Rk is located on the downstream side of each measurement flow path L. The single kind of the protein Ta described above has been fixed to the upstream side linker film Rj. Nothing has been fixed to the downstream side linker film Rk. An inlet hole Lin for injection of the compound solution Ky into each measurement flow path L is located on the upstream side of each measurement flow path L of the analysis vessel U1. An outlet hole Lout for discharging of the compound solution Ky from the measurement flow path L is located on the downstream side of each measurement flow path L of the analysis vessel U1. The analysis vessels U1, U2, U3, and U4 have the identical structures.

Each of the compound solutions Ky1 to Ky3840 described above is injected into one of the measurement flow paths L of one of the analysis vessels U. The measurement is thus made to find the quantity of the binding of each compound K and the protein Ta, which has been fixed to the upstream side linker film Rj. The downstream side linker film Rk does not undergo the binding with each of the compound K1 to K3840.

The binding quantity described above is the quantity of fixation of the compound K to the protein Ta, which has been fixed to the upstream side linker film Rj. The quantity of the fixation of the compound K to the protein Ta is measured in accordance with a mass alteration per unit area, which mass alteration occurs at the surface of the upstream side linker film Rj due to the fixation of the compound K to the protein Ta.

The actual measurement data Dm1 to Dm3840 and the reference measurement data Dr1 to Dr3840 are acquired from the measurement made with respect to the single kind of the protein Ta, which has been fixed to each measurement flow path L, and each of the 3,840 kinds of the compounds K1 to K3840. The screening apparatus 100 having the constitution described above utilizes the values of the actual measurement data Dm1 to Dm3840 and the reference measurement data Dr1 to Dr3840 and extracts the hit compound Hk, which is capable of undergoing the binding with the protein Ta, from the compounds K1 to K3840. The single kind of the protein Ta has been fixed to each of the six measurement flow paths L1 to L6 having been located in each of the analysis vessels U1, U2, U3, and U4 (a total of 24 measurement flow paths).

The screening apparatus 100 is provided with a controller (not shown) for controlling the analysis unit 110 and the screening unit 160. The controller controls the operations, which are performed by the analysis unit 110 and the screening unit 160, and the timings, with which the operations are performed.

How the analysis unit 110 for measuring the quantity of the binding of the protein Ta and the compound with each other operates will be described hereinbelow.

Specifically, firstly, the analysis vessel U1 is conveyed to an analysis position Ps. Also, the laser beam Le is irradiated through a prism surface P28, which is one of the prism surfaces of the prism P25 and is other than the total reflection surface Ls described above, to each of the actual measurement region, at which the upstream side linker film Rj has been formed on the total reflection surface Ls, and the reference measurement region, at which the downstream side linker film Rk has been formed on the total reflection surface Ls. The irradiation of the laser beams Le, Le, . . . is performed such that the laser beam Le may be converged onto each of the actual measurement region and the reference measurement region.

The laser beam Le, which has been irradiated to the actual measurement region, is totally reflected from the actual measurement region. The thus reflected laser beam Le passes through a prism surface P29 of the prism P25 as a divergent laser beam and is radiated out from the prism P25. Also, the laser beam Le, which has been irradiated to the reference measurement region, is totally reflected from the reference measurement region. The thus reflected laser beam Le passes through the prism surface P29 of the prism P25 as a divergent laser beam and is radiated out from the prism P25. (The actual measurement region will hereinbelow be often referred to as the "act" region. Also, the reference measurement region will hereinbelow be often referred to as the "ref" region.)

The actual measurement region is the region on the base body block, to which region the single kind of the ligand has been fixed. The reference measurement region is the region on the base body block, to which region the single kind of the ligand has not been fixed.

Each of the laser beams Le, Le, . . . , which have been radiated out from the prism P25 as the divergent laser beams, passes through one of measuring optical systems Op1 to Op6, which are located respectively for the measurement flow paths L1 to L6. Each of the laser beams Le, Le, . . . thus impinges upon one of measuring sensors 32, 32, . . . , which may be constituted of two-dimensional CCD sensors, or the like. With each of the measuring sensors 32, 32, . . . having received the laser beams Le, Le, . . . , the measurement is made with respect to a position of a dark line occurring at the time at which the laser beam Le has been totally reflected, i.e. the ATR angle due to the surface plasmon resonance. In this manner, the ATR angle at the actual measurement region, to which the protein Ta has been fixed, and the ATR angle at the reference measurement region, to which the protein Ta has not been fixed, are acquired.

Also, the compound solution Ky is caused to flow through the measurement flow path L, and the actual measurement data is acquired in accordance with the quantity of alteration of the ATR angle at the actual measurement region, which has been brought into contact with the compound solution Ky. Also, the reference measurement data is acquired in accordance with the quantity of alteration of the ATR angle at the reference measurement region, which has been brought into contact with the compound solution Ky.

The actual measurement data, which is acquired in accordance with the quantity of alteration of the ATR angle at the actual measurement region, corresponds to the refractive index alteration quantity, which has been caused to occur when the analyte solution has been brought into contact with the actual measurement region on the prism P25 acting as the base body block. Also, the reference measurement data, which is acquired in accordance with the quantity of alteration of the ATR angle at the reference measurement region, corresponds to the refractive index alteration quantity, which has been caused to occur when the analyte solution has been brought into contact with the reference measurement region on the prism P25 acting as the base body block.

Each of data acquiring sections 34, 34, . . . successively receives a signal, which represents the ATR angle at the actual measurement region, and a signal, which represents the ATR angle at the reference measurement region, from the corresponding measuring sensors 32, 32. The data acquiring sections 34, 34, . . . thus acquire the actual measurement data Dm1, Dm2, . . . , each of which represents the quantity of alteration of the ATR angle at the actual measurement region.

Also, the data acquiring sections 34, 34, . . . acquire the reference measurement data Dr1, Dr2, . . . , each of which represents the quantity of alteration of the ATR angle at the reference measurement region.

Each of the data acquiring sections 34, 34, . . . sends a pair of the actual measurement data and the reference measurement data into the storage section 82.

More specifically, when the analysis vessel U1 has been located at the analysis position Ps, a predetermined quantity of each of the compound solutions Ky1 to Ky6, which have been accommodated in the plate PL1, is sucked by one of injection tubes Fi1 to Fi6. The injection tubes Fi1 to Fi6, each of which has sucked one of the compound solutions Ky1 to Ky6, are conveyed and inserted into the inlet holes Lin of the measurement flow paths L1 to L6, respectively. The compound solutions Ky1 to Ky6 are injected respectively from the injection tubes Fi1 to Fi6 into the measurement flow paths L1 to L6. Also, the measurement is made for acquiring the actual measurement data Dm1, Dm2, . . . and the reference measurement data Dr1, Dr2, . . . .

The compound solutions Ky, which have been injected respectively into the measurement flow paths L1 to L6, are capable of being discharged from the measurement flow paths L1 to L6 by suction with discharging tubes Fo1 to Fo6, which have been inserted into the outlet holes Lout. The solution, which is caused to flow through each of the measurement flow paths L1 to L6, is thus capable of being changed over. Therefore, a pre-processing liquid or a post-processing liquid for the measurement is capable of being caused to flow through each of the measurement flow paths L1 to L6.

At the analysis position Ps, the laser beams Le, Le, . . . are respectively irradiated to the actual measurement regions and the reference measurement regions of the measurement flow paths L1 to L6 of the analysis vessel U1. A total of 12 measuring sensors 32, 32, . . . , each of which has been located for each of the actual measurement regions and the reference measurement regions, measure the ATR angles described above.

When the measurement with respect to the compound solutions Ky1 to Ky6 has been finished, restoring processing is performed for restoring the measurement flow paths L1 to L6 of the analysis vessel U1 to the state prior to the measurement. Specifically, as for the compound having undergone the binding with the protein Ta at the actual measurement region, the protein Ta is released from the binding with the compound, and the compound is removed. Also, the compound solutions Ky1 to Ky6, the buffer solution, and the like, which remain on the actual measurement regions, the reference measurement regions, and wall surfaces of the measurement flow paths L1 to L6, are washed and removed.

After the aforesaid restoring processing has been performed on the analysis vessel U1, the second measurement with the analysis vessel U1 is made with respect to the compound solutions Ky7 to Ky12.

In the manner described above, the restoring processing is performed on the analysis vessel U1 after the analysis vessel U1 has been used one time for the measurement. The analysis vessel U1 is used 160 times for making the measurement with respect to the compound solutions Ky1 to Ky960. The actual measurement data Dm1 to Dm960 and the reference measurement data Dr1 to Dr960 are thus acquired from the measurement with respect to the compound solutions Ky1 to Ky960.

After the analysis vessel U1 has been used 160 times for making the measurement, the analysis vessel U1 is conveyed out of the analysis position Ps, and the next analysis vessel U2 is located at the analysis position Ps.

In the same manner as that described above, the analysis vessel U2 is used 160 times for the measurement. Each of the compound solutions Ky961 to Ky1920 is caused to flow through one of the measurement flow paths L1 to L6 of the analysis vessel U2, and the measurement is made with respect to the protein Ta and each of the compounds K961 to K1920. The actual measurement data Dm961 to Dm1920 and the reference measurement data Dr961 to Dr1920 are thus acquired from the measurement with respect to the compound solutions Ky961 to Ky1920.

As for each of the analysis vessels U3 and U4, the measurement is performed in the same manner as that described above. From the measurement having been made by use of the analysis vessels U1, U2, U3, and U4, the actual measurement data Dm1 to Dm3840, each of which represents the quantity of the binding of the protein Ta and one of the compounds K1 to K3840 with each other, and the reference measurement data Dr1 to Dr3840 are acquired. At this stage, a day's measurement is finished.

The actual measurement data Dm1 to Dm3840 and the reference measurement data Dr1 to Dr3840 having been acquired in the manner described above are sent from the analysis unit 110 into the screening unit 160.

It is presumed previously that the majority of the actual measurement data Dm1 to Dm3840 are the actual measurement data having been obtained in the state, in which the protein Ta and the compound are not capable of undergoing the binding with each other. Also, it is presumed previously that the actual measurement data having been obtained in the state, in which the protein Ta and the compound have undergone the binding with each other, are approximately 1% of the whole actual measurement data and are at most 2% of the whole actual measurement data.

As for the measurement of the quantity of the binding of the protein Ta and the compound, in which the attenuated total reflection is utilized, reference may be made to, for example, "Methods of Experiments and Real-Time Analysis of Interaction with Biological Materials" by Kazuhiro Nagata & Hiroshi Handa, published by Springer Verlag Tokyo K.K.

The operation of the screening unit 160 for enhancing the reliability of the screening operation, such that the efficiency of the screening operation may not become low, will be described hereinbelow.

Figure 3:
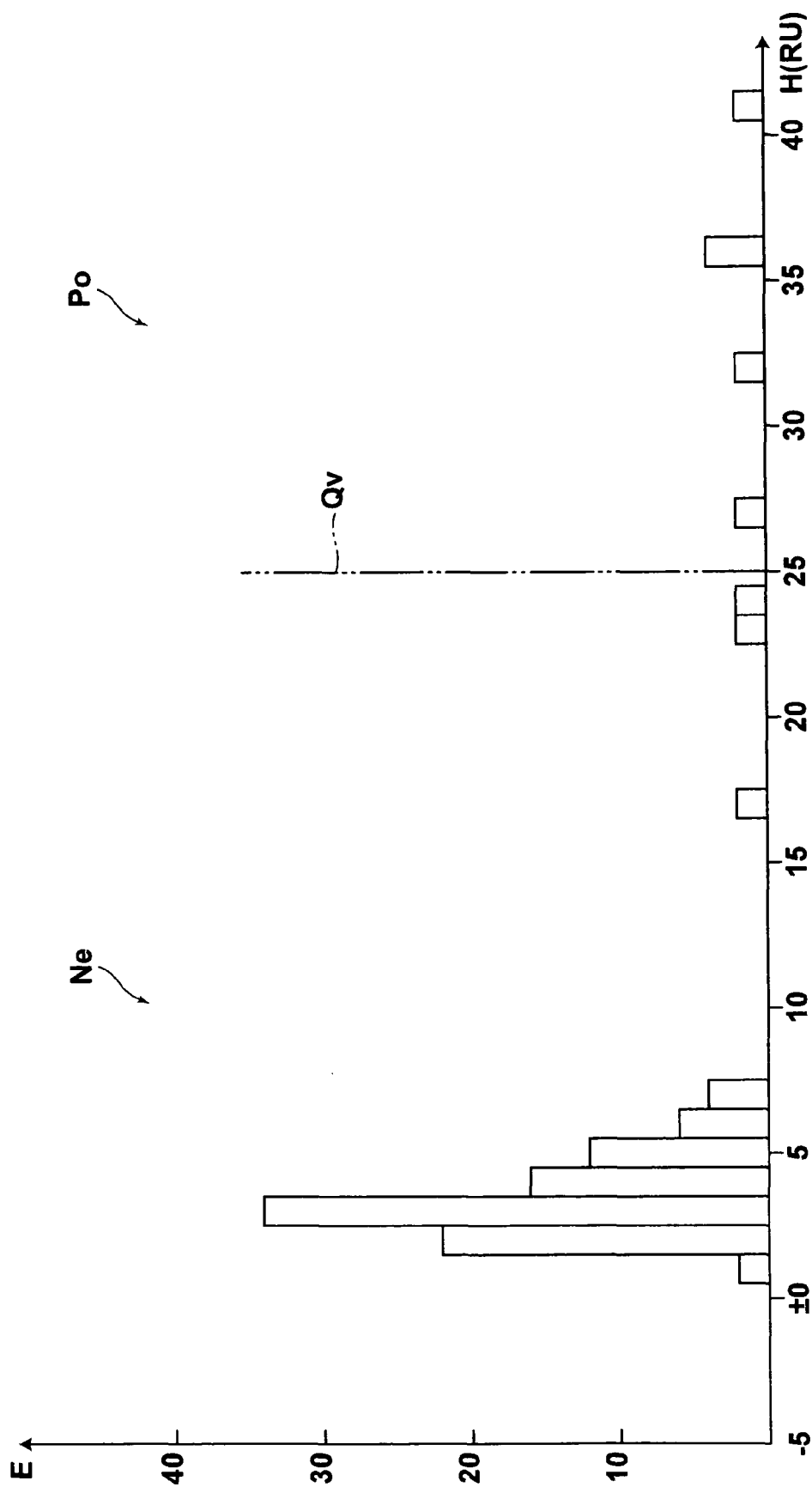
FIG. 3 is a graph showing a histogram of 3,840 pieces of unprocessed binding quantity data.

FIG. 3 is a graph showing a histogram of 3,840 pieces of unprocessed binding quantity data. In FIG. 3, a vertical axis E represents the frequency of occurrence, and a horizontal axis H represents the binding quantity (in units of RU). Each of the values of the unprocessed binding quantity data Dv, which are shown in FIG. 3, fundamentally represents the binding quantity per unit area between the protein Ta and the compound K at the actual measurement region. Therefore, each of the values of the unprocessed binding quantity data Dv is represented in units of RU (resonance unit).

The pre-processing section 83 receives the actual measurement data Dm1, Dm2, ... and the reference measurement data Dr1, Dr2, ... from the storage section 82. The pre-processing section 83 subtracts each of the values of the reference measurement data Dr1, Dr2, ... from the corresponding one of the values of the actual measurement data Dm1, Dm2, ... and thereby acquires the unprocessed binding quantity data Dv1, Dv2, ....

As illustrated in FIG. 3, the majority of the values of the unprocessed binding quantity data Dv, i.e. the values of the binding quantity (RU) plotted on the horizontal axis H, are located in the vicinity of 0 RU. There is a strong probability that the compounds, which are associated with the binding quantity (RU) close to 0 RU, will be the compounds which are not capable of undergoing the binding with the protein Ta. Also, there is a strong probability that a small number of compounds, which are associated with the values of the unprocessed binding quantity data Dv plotted in the region spaced apart from 0 RU to the plus side, will be the compounds which are capable of undergoing the binding with the protein Ta.

In cases where the compound K and the protein Ta have not undergone the binding with each other, the value of the unprocessed binding quantity data Dv will fundamentally become equal to 0. Specifically, in cases where the compound K and the protein Ta have not undergone the binding with each other, the value of the unprocessed binding quantity data Dv, which is obtained by subtracting the value of the reference measurement data Dr from the value of the corresponding actual measurement data Dm, will fundamentally become equal to 0.

However, actually, it may often occur that, in cases where the compound K and the protein Ta have not undergone the binding with each other, the value of the unprocessed binding quantity data Dv does not become equal to 0. The value of the unprocessed binding quantity data Dv varies in accordance with the value of the reference measurement data Dr. Specifically, the value of the reference measurement data Dr substantially corresponds to the refractive index of the compound solution Ky. Therefore, the value of the unprocessed binding quantity data Dv, which is obtained in cases where the compound K and the protein Ta have not undergone the binding with each other, varies in accordance with the refractive index of the compound solution Ky, which has been used for the measurement of the unprocessed binding quantity data Dv. The details of the variation components, which vary in accordance with the values of the reference measurement data Dr, will be described later.

In this embodiment, each of the values of the variation components, each of which is contained in one of the unprocessed binding quantity data Dv, is subtracted from the corresponding one of the values of the unprocessed binding quantity data Dv. In this manner, the processed binding quantity data Dw, each of which represents more accurately the quantity of the binding of the protein Ta and the compound K at the actual measurement region, are thereby acquired. How the processed binding quantity data Dw are acquired will be described hereinbelow.

Figure 4:
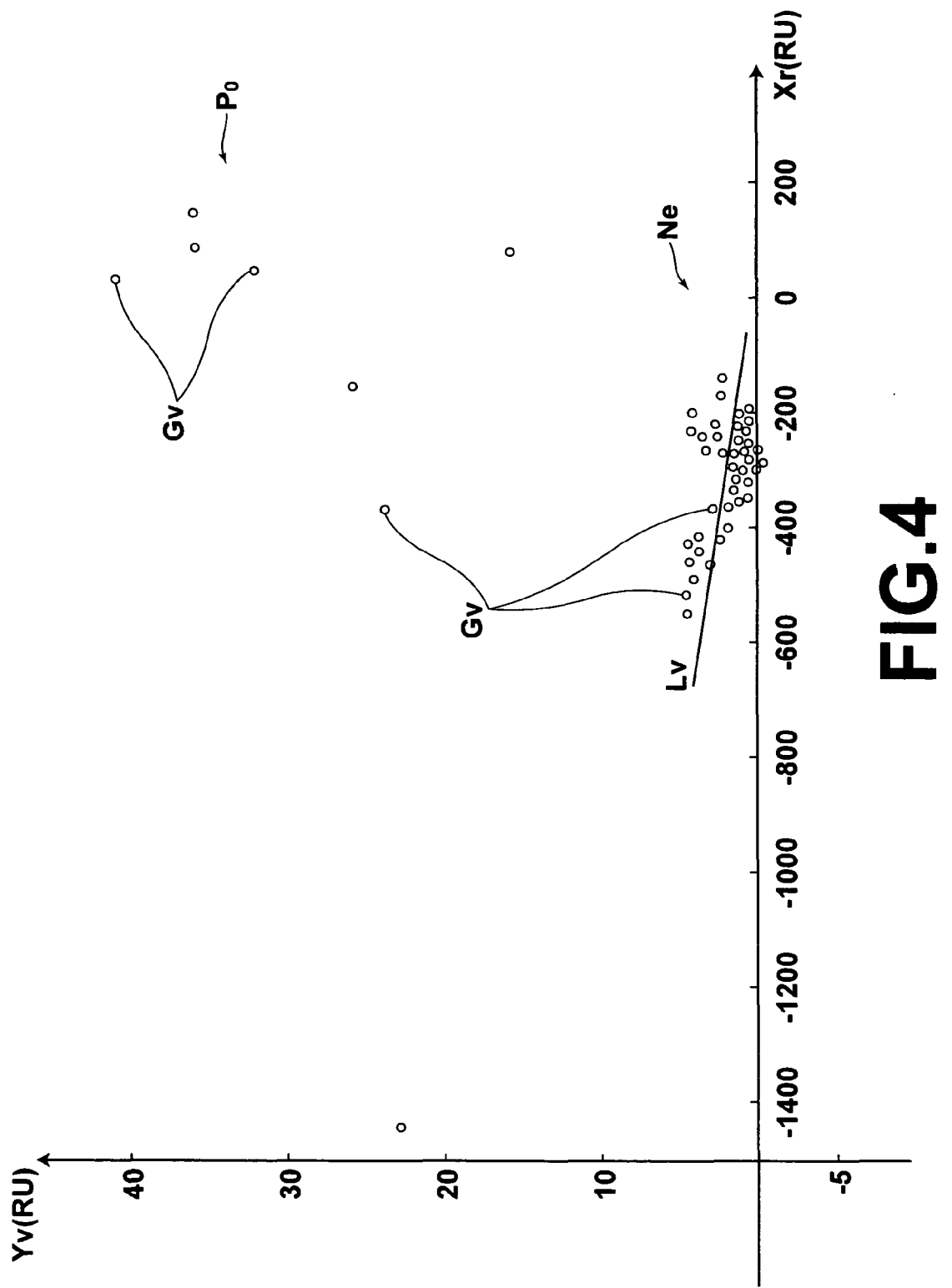
FIG. 4 is a graph showing corresponding points, each of which is defined by a combination of each of values of reference measurement data and each of values of unprocessed binding quantity data.
Figure 5:
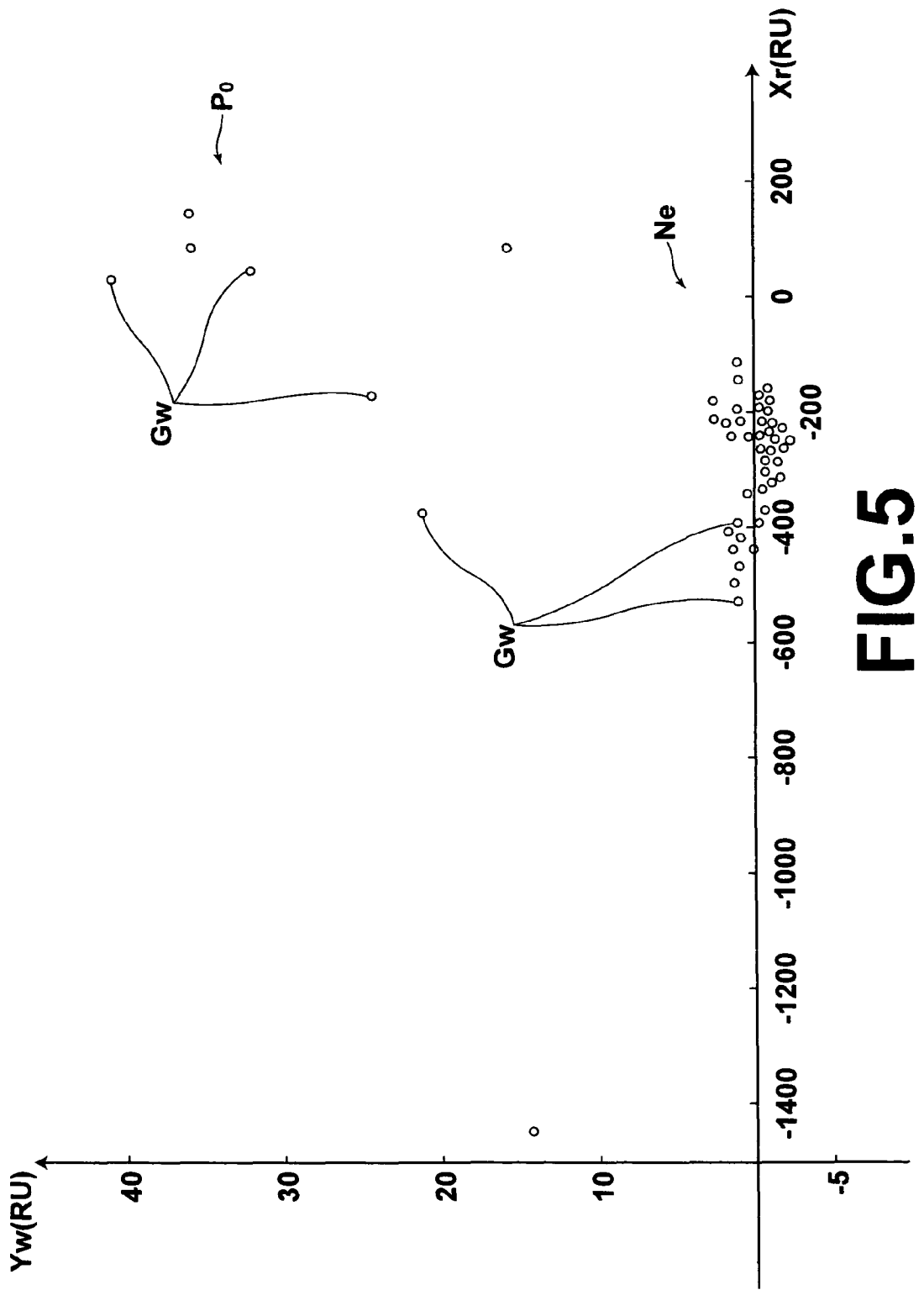
FIG. 5 is a graph showing corresponding points, each of which is defined by a combination of each of values of reference measurement data and each of values of processed binding quantity data.
Figure 6:
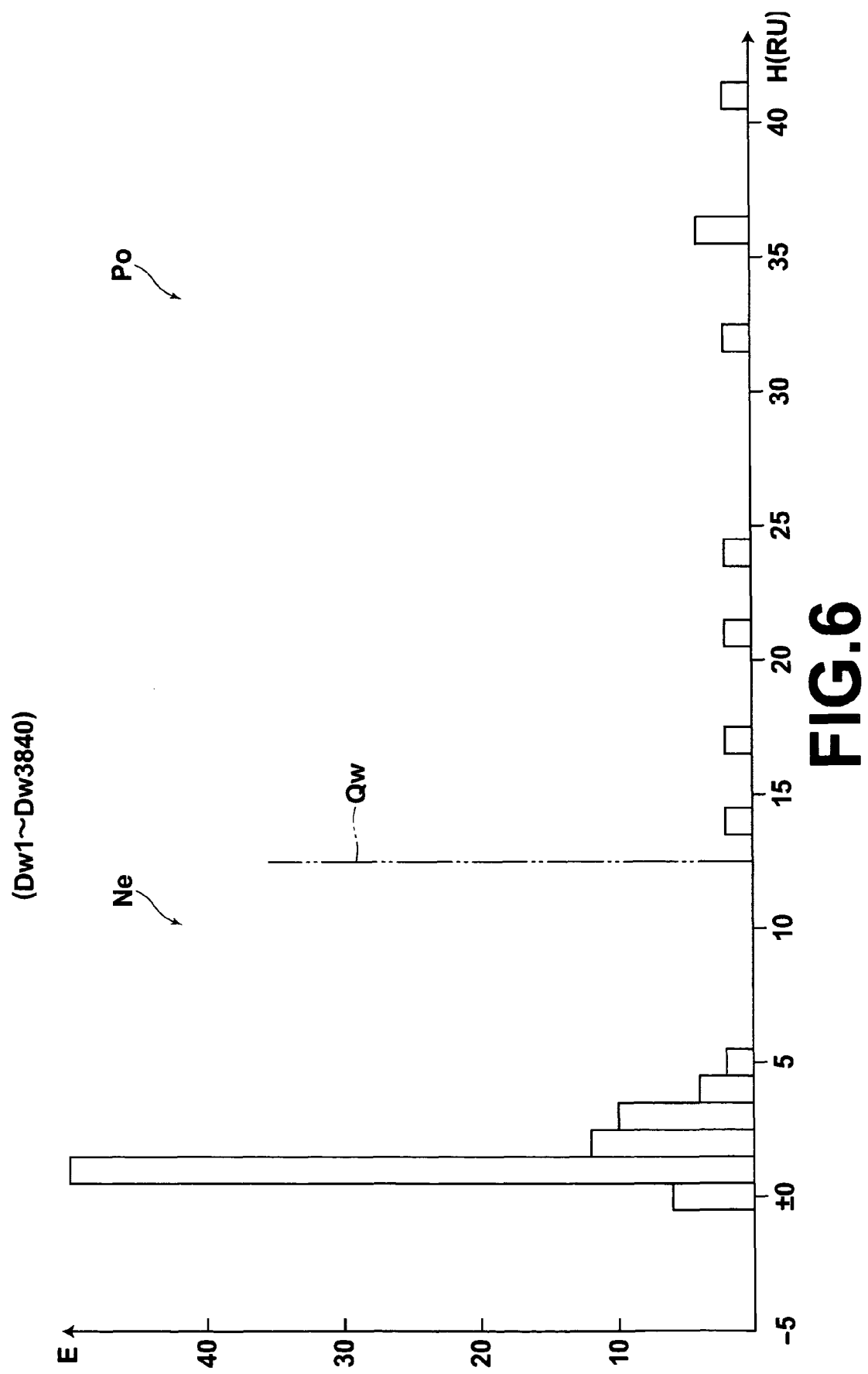
FIG. 6 is a graph showing a histogram of 3,840 pieces of processed binding quantity data.

FIG. 4 is a graph showing corresponding points, each of which is defined by a combination of each of values of reference measurement data and each of values of unprocessed binding quantity data. In FIG. 4, a vertical axis Yv represents the values of the unprocessed binding quantity data Dv, and a horizontal axis Xr represents the values of the reference measurement data Dr. Also, corresponding points Gv, each of which is defined by the combination of the value of the reference measurement data Dr and the value of the unprocessed binding quantity data Dv having been obtained from the measurement for each of the compound solutions Ky1 to Ky3840, are plotted on the coordinate system of FIG. 4. FIG. 5 is a graph showing corresponding points, each of which is defined by a combination of each of values of reference measurement data and each of values of processed binding quantity data. In FIG. 5, a vertical axis Yw represents the values of the processed binding quantity data Dw, and a horizontal axis Xr represents the values of the reference measurement data Dr. Also, corresponding points Gw, each of which is defined by the combination of the value of the reference measurement data Dr and the value of the processed binding quantity data Dw having been obtained from the measurement for each of the compound solutions Ky1 to Ky3840, are plotted on the coordinate system of FIG. 5. FIG. 6 is a graph showing a histogram of 3,840 pieces of processed binding quantity data. In FIG. 6, the vertical axis E represents the frequency of occurrence, and the horizontal axis H represents the processed binding quantity (in units of RU). The histogram of the 3,840 pieces of the processed binding quantity data Dw is shown on the coordinate system of FIG. 6.

In FIG. 4, the values of the corresponding points Gv plotted on the vertical axis Yv are the values of the unprocessed binding quantity data Dv, which have been converted into the RU values. Also, in FIG. 4, the values of the corresponding points Gv plotted on the horizontal axis Xr are the values of the reference measurement data Dr representing the refractive indexes of the compound solutions Ky, which values have been converted formally into the RU values. In FIG. 5, the values of the corresponding points Gw plotted on the vertical axis Yw are the values of the processed binding quantity data Dw, which have been converted into the RU values. Also, in FIG. 5, the values of the corresponding points Gw plotted on the horizontal axis Xr are the values of the reference measurement data Dr representing the refractive indexes of the compound solutions Ky, which values have been converted formally into the RU values.

In FIG. 4, a group Ne is constituted of the corresponding points Gv having the values of the unprocessed binding quantity data Dv, which values are located in the vicinity of 0 RU. As for the group Ne, there is a strong probability that the compound will be the compound which has not undergone the binding with the protein Ta. Also, in FIG. 4, a group Po is constituted of the corresponding points Gv having the values of the unprocessed binding quantity data Dv, which values are spaced apart from 0 RU. As for the group Po, there is a strong probability that the compound will be the compound which has undergone the binding with the protein Ta.

As illustrated in FIG. 4, attention is given to the corresponding points Gv belonging to the group Ne, which has a strong probability of being the compound having not undergone the binding with the protein Ta, and a variation component approximate curve Lv, which approximately represents the corresponding points Gv by a curve or a straight line, is obtained. (In FIG. 4, the variation component approximate curve Lv is represented by Lv.) The variation component approximate curve Lv represents the variation components $\delta$, which vary in accordance with the magnitudes of the values of the reference measurement data Dr. The variation component approximate curve Lv may approximately represent the corresponding points Gv by a curve or a straight line.

Thereafter, reference is made to the variation component approximate curve Lv, and calculation is made to find each of the variation components $\delta 1$ to $\delta 3840$, each of which is contained in one of the unprocessed binding quantity data Dv1 to Dv3840 and corresponds to one of the reference measurement data Dr1 to Dr3840 having been acquired in cases where each of the compounds K and the protein Ta have not undergone the binding with each other and in cases where each of the compounds K and the protein Ta have undergone the binding with each other. Also, each of the values of the variation components $\delta 1$ to $\delta 3840$, each of which is contained in one of the unprocessed binding quantity data Dv1 to Dv3840, is subtracted from the corresponding one of the values of the unprocessed binding quantity data Dv1 to Dv3840, and the processed binding quantity data Dw1 to Dw3840 are thereby acquired. The thus acquired processed binding quantity data Dw1 to Dw3840 are utilized as the binding quantity data for use in extracting the compound K, which is capable of undergoing the binding with the protein Ta.

As illustrated in FIG. 5, of the corresponding points Gw, each of which is defined by the combination of each of the values of the reference measurement data Dr1 to Dr3840 and each of the values of the processed binding quantity data Dw1 to Dw3840, the dispersion of the values of the Yw coordinates (i.e., the values of the processed binding quantity data Dw) of the corresponding points Gw, which belong to the group Ne and have the values of the processed binding quantity data Dw located in the vicinity of 0 RU, is suppressed.

Also, as illustrated in FIG. 6, in cases where the processed binding quantity data Dw1 to Dw3840 are illustrated as the histogram, the data, which are of the compounds having a strong probability of being the compounds having not undergone the binding with the protein Ta, are centralized upon the vicinity of 0 RU to a higher extent than in the histogram of FIG. 3, which histogram represents the unprocessed binding quantity data Dv1 to Dv3840 having been obtained by simply subtracting the reference measurement data Dr from the actual measurement data Dm. Therefore, in cases where the processed binding quantity data Dw1 to Dw3840 are utilized, the discrimination is capable of being made more clearly between the binding quantity data on the compounds having undergone the binding with the protein Ta and the binding quantity data on the compounds having not undergone the binding with the protein Ta.

The variation components $\delta$, which are subtracted from the values of the unprocessed binding quantity data Dv, will hereinbelow be described in detail.

Each of the variation components $\delta$ described above is caused to occur due to the conditions such that the protein Ta has been fixed to the upstream side linker film Rj at the "act" region (i.e., the actual measurement region) and such that nothing has been fixed to the downstream side linker film Rk at the "ref" region (i.e., the reference measurement region). Specifically, the effect of the compound solution Ky, which the "act" region receives, is smaller by the extent corresponding to the volume of the protein Ta than the effect of the compound solution Ky, which the "ref" region receives. Therefore, in cases where the compound K and the protein Ta do not undergo the binding with each other, the value of the unprocessed binding quantity data Dv, which is obtained by subtracting the value of the reference measurement data Dr at the "ref" region from the value of the actual measurement data Dm at the "act" region, does not become equal to 0 and varies in accordance with the value of the reference measurement data Dr. Accordingly, in cases where the value of the reference measurement data Dr is subtracted from the value of the corresponding actual measurement data Dm, the effect of the expelling volume of the protein Ta, i.e. the variation component $\delta$ contained in the value of the unprocessed binding quantity data Dv, is not capable of being canceled.

The variation component $\delta$ will hereinbelow be explained by use of formulas. Firstly, variables are defined as shown below.

Act(i): The dark line position obtained from the measurement at the "act" region.

Ref(i): The dark line position obtained from the measurement at the "ref" region.

f(n): The dark line position at the time of the refractive index n.

Bind(i): The quantity of the binding with the protein (in units of refractive index).

bulk(i): The refractive index of the buffer solution constituting the compound solution.

Hai(i): The volume of the protein expelling the buffer solution.

In cases where the protein is absent, the value of Hai(i) is equal to 0. In cases where the buffer solution is absent, and only the protein is present, the value of Hai(i) is equal to 1.

In cases where the variables are defined in the manner described above, Act(i) and Ref(i) may be represented by the formulas shown below.

$$Act(i)=f(Bind(i)+bulk(i)\times(1-Hai(i)))$$

$$Ref(i)=f(bulk(i))$$

Therefore, the value of Act(i)-Ref(i) may be represented by the formula shown below.

$$Act(i)-Ref(i)=f(Bind(i)-bulk(i)\times Hai(i))$$

In cases where the binding does not occur, i.e. in cases where Bind(i)=0, the formula shown below obtains.

$$Act(i)-Ref(i)=f(-bulk(i)\times Hai(i))$$

Thus, in such cases, the value of Act (i)–Ref(i) does not become equal to 0.

The value of f(−bulk(i)×Hai(i)) shown above is the principal constituent of the variation component δ.

In FIG. 4, the vertical axis Yv represents the value of the formula:

$$Act(i)-Ref(i)=f(Bind(i)-bulk(i)\times Hai(i))$$

Also, in FIG. 4, the horizontal axis Xr represents the value of the formula:

$$Ref(i)=f(bulk(i))$$

As for the group Ne, which has a strong probability of being the compound having not undergone the binding with the protein Ta, it may be regarded that Bind(i)=0. Therefore, as for the group Ne, it may be regarded that the vertical axis Yv represents the value of f (−bulk (i)×Hai (i)).

Therefore, as for the group Ne, it may be regarded that the vertical axis Yv represents the value of f(−bulk(i)×Hai(i)), which corresponds to the variation component δ. Specifically, it may be regarded that the variation component approximate curve Lv shown in FIG. 4 represents the relationship between the value of the reference measurement data Dr, which corresponds to the value of Ref(i), and the value of the variation component δ.

Accordingly, the value of the variation component δ, which varies in accordance with the value of the reference measurement data Dr, is capable of being calculated by use of the variation component approximate curve Lv.

How the screening unit 160 performs the aforesaid technique will be described hereinbelow with reference to FIG. 1.

The variation relationship acquiring section 84 receives the reference measurement data Dr1, Dr2, . . . from the storage section 82. The variation relationship acquiring section 84 also receives the unprocessed binding quantity data Dv1, Dv2, . . . from the pre-processing section 83. Also, the variation relationship acquiring section 84 calculates a mean value Mv of the values of the unprocessed binding quantity data Dv1, Dv 2, . . . . Further, the variation relationship acquiring section 84 calculates a standard deviation σv, which represents the dispersion of the values of the unprocessed binding quantity data Dv1, Dv2, . . . . Furthermore, the variation relationship acquiring section 84 extracts the unprocessed binding quantity data Dv falling within the range of from the value, which takes a position located at a spacing three times as large as the standard deviation σv from the mean value Mv toward the plus side, to the value, which takes a position located at a spacing three times as large as the standard deviation σv from the mean value Mv toward the minus side, (i.e. falling within the range of Mv±3σv) as the unprocessed binding quantity data Dv belonging to the group Ne described above. Also, the variation relationship acquiring section 84 calculates a function F representing the variation component approximate curve Lv approximately representing the corresponding points Gv, each of which is defined by the combination of the value of the unprocessed binding quantity data Dv belonging to the group Ne and the value of the reference measurement data Dr corresponding to the unprocessed binding quantity data Dv. The variation component approximate curve Lv approximately represents the corresponding points Gv by a curve or a straight line.

The thus obtained function F represents the relationship between the value of the reference measurement data Dr and the value of the variation component δ, which is contained in the unprocessed binding quantity data Dv corresponding to the reference measurement data Dr. In accordance with the function F, the value of the variation component δ corresponding to the reference measurement data Dr is capable of being calculated. The relationship δ=F(Dr) represented by the function F is capable of being applied commonly to the data, which are obtained in cases where the compound K and the protein Ta have not undergone the binding with each other, and the data, which are obtained in cases where the compound K and the protein Ta have undergone the binding with each other.

The variation component acquiring section 85 receives the information, which represents the function F, from the variation relationship acquiring section 84. By use of the function F, the variation component acquiring section 85 calculates the variation components δ1 to δ3840, each of which corresponds to one of the reference measurement data Dr1 to Dr3840 belonging to the group Ne and the group Po.

The processed binding quantity acquiring section 86 receives the information, which represents the values of the variation components δ1 to δ3840 having been calculated by the variation component acquiring section 85. The processed binding quantity acquiring section 86 also receives the information, which represents the values of the unprocessed binding quantity data Dv1 to Dv3840. Further, the processed binding quantity acquiring section 86 subtracts each of the values of the variation components δ1 to δ3840, each of which is contained in one of the unprocessed binding quantity data Dv1 to Dv3840, from the corresponding one of the values of the unprocessed binding quantity data Dv1 to Dv3840. In this manner, the processed binding quantity data Dw1 to Dw3840 are acquired. The value of the processed binding quantity data Dw is capable of being calculated from the relationship:

$$Dw=Dv-\delta=Dv-F(Dr)$$

Furthermore, the threshold value setting section 87 sets the threshold value Qw, which is to be used for the extraction of the hit compound Hk, by use of the processed binding quantity data Dw1 to Dw3840 having been acquired by the processed binding quantity acquiring section 86. Specifically, the threshold value setting section 87 calculates a means value Mw and a standard deviation σw of the values of the processed binding quantity data Dw1 to Dw3840. Also, the threshold value setting section 87 sets the value, which takes a position located at a spacing three times as large as the standard deviation σw from the mean value Mw toward the plus side, as the threshold value Qw. More specifically, the threshold value Qw is calculated with the formula:

$$Qw=Mw+(3\times\sigma w)$$

Thereafter, the hit compound extracting section 88 makes a comparison between the threshold value Qw and each of the values of the processed binding quantity data Dw1 to Dw3840. The hit compound extracting section 88 extracts the compound corresponding to the processed binding quantity data Dw, which has the value larger than the threshold value Qw, as the hit compound Hk. The thus extracted hit compound Hk is displayed on a display device 50.

In the variation relationship acquiring section 84 described above, the unprocessed binding quantity data Dv falling within the aforesaid range of Mv±3σv have been used for the calculation of the function F representing the variation relationship. All of the unprocessed binding quantity data Dv falling within the range of Mv±3σv will not necessarily be the data obtained in cases where the compound K and the protein Ta have not undergone the binding with each other. However, it is capable of being presumed previously that the quantity of the unprocessed binding quantity data Dv falling within the aforesaid range of Mv±3σv, which data may be obtained in cases where the compound K and the protein Ta have undergone the binding with each other, will be markedly small, and that the effect of such unprocessed binding quantity data Dv will be markedly small. Therefore, in the screening operation, the effect of such unprocessed binding quantity data Dv is capable of being ignored substantially.

As illustrated in FIG. 6, with the screening technique utilizing the processed binding quantity data Dw1 to Dw3840 free from the variation components δ in accordance with the present invention, the mean value Mw of the values of the processed binding quantity data Dw1 to Dw3840 is equal to 2.1 RU, and the value of the standard deviation σw is equal to 3.4 RU. Therefore, the threshold value Qw (=Mw+3×σw) is capable of being set at 12.3 RU, and the hit compound Hk is thereby capable of being extracted.

However, as illustrated in FIG. 3, with the screening technique utilizing the unprocessed binding quantity data Dv1 to Dv3840 containing the variation components δ in accordance with the conventional technique, the mean value Mv of the values of the unprocessed binding quantity data Dv1 to Dv3840 is equal to 3.7 RU, and the value of the standard deviation σv is equal to 7.1 RU. Therefore, in such cases, the threshold value Qv (=Mv+3×σv) is set at 25.0 RU, and the hit compound is thereby extracted.

As described above, with the screening apparatus 100 in accordance with the present invention, the screening operation is performed by use of the processed binding quantity data Dw1 to Dw3840 free from the variation components δ, each of which data more accurately represents the quantity of the binding of the protein Ta and the compound K with each other. Therefore, the hit compound Hk is capable of being extracted more accurately.

With the screening apparatus 100, a day's measurement is made in the manner described above. Alternatively, for example, the measurement described above may be iterated for three days with respect to the single kind of the protein Ta, and 11,520 times (3,840 times×3 days) of measurement may be performed. The screening operation for extracting a hit compound, which is capable of undergoing the binding with the single kind of the protein Ta, from 11,520 kinds of the compounds may thus be performed.

In such cases, for example, the measurement conditions may alter every day for an apparatus adjustment. In such cases, the screening operation should preferably be performed in the manner described below. Specifically, the variation component approximate curve representing the variation components is calculated every day with respect to the 3,840 pieces of data having been obtained in one day. Also, the 3,840 pieces of the processed binding quantity data are obtained every day by use of each variation component approximate curve. Thereafter, the screening operation is performed by setting one threshold value with respect to all of 11,520 pieces of the processed binding quantity data, which have been obtained over three days.

Also, for example, in cases where the measurement is performed under identical measurement conditions over three days, one variation component approximate curve, which represents the variation components, may be calculated by use of 11,520 pieces of data having been obtained from three day's measurement. Also, 11,520 pieces of processed binding quantity data may be obtained by use of the thus calculated variation component approximate curve. Further, the screening operation may be performed by setting one threshold value with respect to all of 11,520 pieces of the processed binding quantity data.

In the embodiment described above, the threshold value is set in accordance with the standard deviation of the values of the processed binding quantity data. Alternatively, the threshold value may be set by use of one of various other techniques.

Also, in the embodiment described above, the analyte, which is capable of undergoing the binding with the single kind of the ligand, is extracted from the multiple kinds of the analytes and in accordance with the quantity of the binding of the single kind of the ligand and each of the multiple kinds of the analytes with each other. The screening method in accordance with the present invention is also applicable to the screening operation, wherein a ligand, which is capable of undergoing the binding with a single kind of an analyte, is extracted from the multiple kinds of the ligands and in accordance with the quantity of the binding of the single kind of the analyte and each of the multiple kinds of the ligands with each other.

Figure 7:
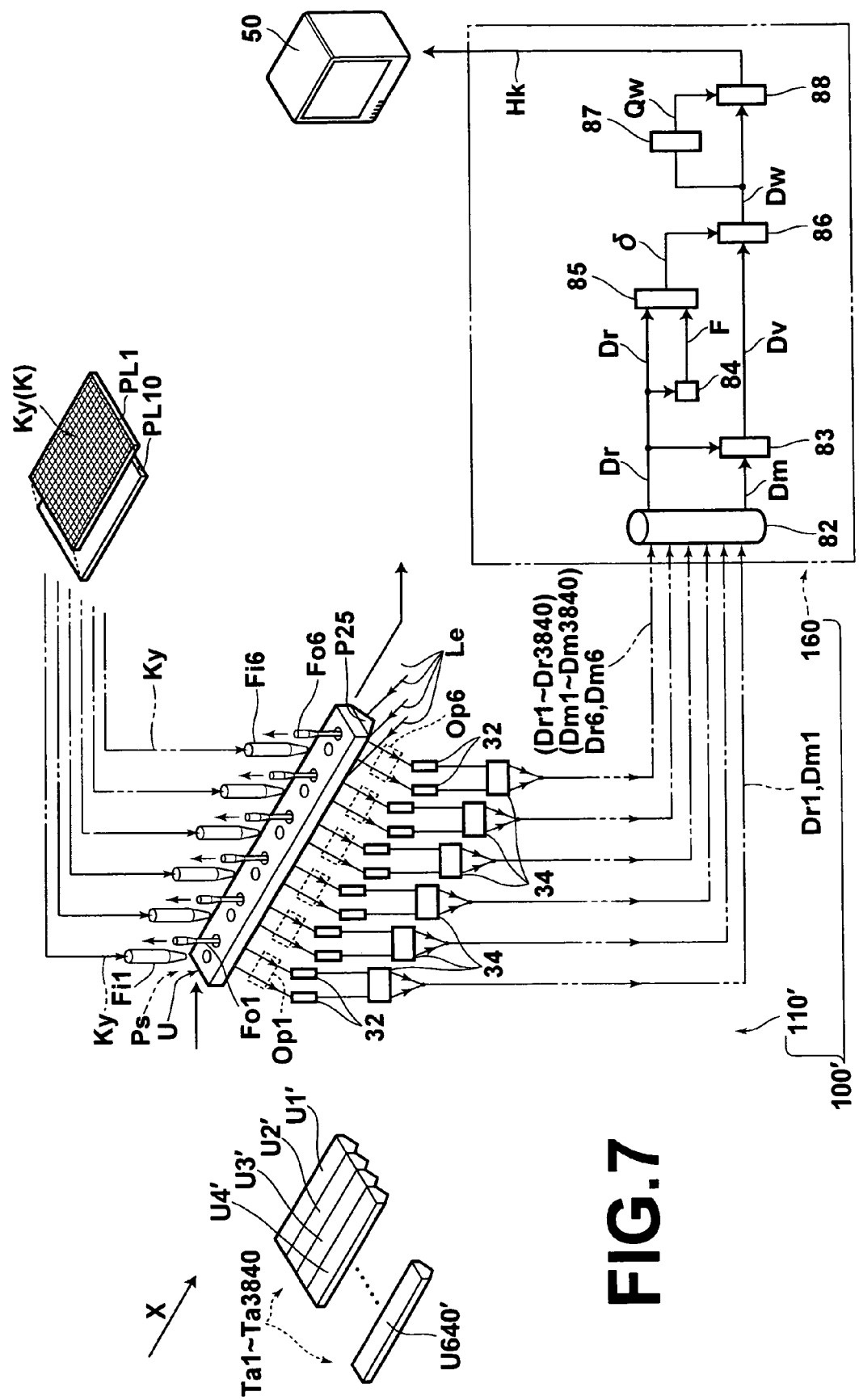
FIG. 7 is a conceptual view showing a different embodiment of the screening apparatus for carrying out a different embodiment of the screening method in accordance with the present invention.

FIG. 7 is a conceptual view showing a different embodiment of the screening apparatus for carrying out a different embodiment of the screening method in accordance with the present invention, in which a screening operation is performed in accordance with the quantity of the binding of a single kind of an analyte and each of multiple kinds of ligands with each other. A screening apparatus 100' illustrated in FIG. 7 is constituted basically in the same manner as that for the screening apparatus 100 of FIG. 1, except that each of different kinds of proteins Ta1 to Ta3840 has been fixed to one of a total of 3,840 actual measurement regions of analysis vessels U1' to U640', and except that a compound solution Ky containing a single kind of a compound K is accommodated in the plates PL1 to PL10. In FIG. 7, similar elements are numbered with the same reference numerals with respect to FIG. 1.

The screening apparatus 100' for carrying out the different embodiment of the screening method in accordance with the present invention performs the measurement utilizing the attenuated total reflection and acquires processed binding quantity data Dw1 to Dw3840. Each of the processed binding quantity data Dw1 to Dw3840 represents the quantity of the binding of the compound K, which acts as the single kind of the analyte, and each of the proteins Ta1 to Ta3840, which act as the multiple kinds of the ligands, with each other. (The processed binding quantity data Dw1 to Dw3840 will hereinbelow be collectively referred to also as the processed binding quantity data Dw. Also, the proteins Ta1 to Ta3840 will hereinbelow be collectively referred to also as the protein Ta.) Also, the screening apparatus 100' extracts a protein Ta, which is capable of undergoing the binding with the compound K, from the multiple kinds of the proteins Ta1 to Ta3840 and in accordance with the processed binding quantity data Dw1 to Dw3840.

The screening apparatus 100' is provided with an analysis unit 110', which acts as the analysis section. In the analysis unit 110', the compound solution Ky containing the single kind of the compound K is brought into contact with each of the actual measurement regions of the prisms P25, P25, . . . of the analysis vessels U1' to U640', to each of which regions one of the multiple kinds of the proteins Ta1 to Ta3840 has been fixed. The values of actual measurement data Dm1 to Dm3840, which represent the ATR angles, are obtained from the operation for bringing the compound solution Ky into contact with each of the actual measurement regions of the analysis vessels U1' to U640'. Also, the compound solution Ky is brought into contact with each of the reference measurement regions of the prisms P25, P25, . . . of the analysis vessels U1' to U640'. The values of reference measurement data Dr1 to Dr3840, each of which represents the ATR angle and corresponds to one of the actual measurement data Dm1 to Dm3840, are obtained from the operation for bringing the compound solution Ky into contact with each of the reference measurement regions of the analysis vessels U1' to U640'. (The actual measurement data Dm1 to Dm3840 will hereinbelow be collectively referred to also as the actual measurement data Dm. Also, the reference measurement data Dr1 to Dr3840 will hereinbelow be collectively referred to also as the reference measurement data Dr.)

Each of the analysis vessels U1' to U640' is provided with the six actual measurement regions. Each of the different kinds of the proteins Ta1 to Ta3840 has been fixed to one of the total of 3,840 actual measurement regions. Also, each of the analysis vessels U1' to U640' is provided with the six reference measurement regions, each of which corresponds to one of the six actual measurement regions described above. Further, the single kind of the compound solution Ky, which contains the single kind of the compound K, has been accommodated in the plates PL1 to PL10.

The screening apparatus 100' is also provided with the screening unit 160, which acts as the screening section. In the screening unit 160, the storage section 82 stores the actual measurement data Dm1 to Dm3840 and the reference measurement data Dr1 to Dr3840. Also, the pre-processing section 83 subtracts each of the values of the reference measurement data Dr1 to Dr3840 from the corresponding one of the values of the actual measurement data Dm1 to Dm3840 and thereby acquires unprocessed binding quantity data Dv1 to Dv3840. (The unprocessed binding quantity data Dv1 to Dv3840 will hereinbelow be collectively referred to also as the unprocessed binding quantity data Dv.)

Thereafter, the variation relationship acquiring section 84 calculates the relationship F between the values of the reference measurement data Dr and the values of the unprocessed binding quantity data Dv, which vary in accordance with the values of the reference measurement data Dr, the values of the reference measurement data Dr and the values of the unprocessed binding quantity data Dv having been acquired in cases where each of the proteins Ta and the compound K not undergone the binding with each other. Also, the variation component acquiring section 85 makes the calculation in accordance with the aforesaid relationship F to find each of variation components $\delta$1 to $\delta$3840, each of which is contained in one of the unprocessed binding quantity data Dv1 to Dv3840 and corresponds to one of the reference measurement data Dr1 to Dr3840 having been acquired in cases where each of the proteins Ta and the compound K have not undergone the binding with each other and in cases where each of the proteins Ta and the compound K have undergone the binding with each other. (The variation components $\delta$1 to $\delta$3840 will hereinbelow be collectively referred to also as the variation component $\delta$.) Further, the processed binding quantity acquiring section 86 subtracts each of the values of the variation components $\delta$1 to $\delta$3840, each of which is contained in one of the unprocessed binding quantity data Dv1 to Dv3840, from the corresponding one of the values of the unprocessed binding quantity data Dv1 to Dv3840 and thereby acquires processed binding quantity data Dw1 to Dw3840.

Thereafter, the threshold value setting section 87 sets a threshold value Qw, which is to be used for the extraction of the hit compound (in this case, the hit protein) Hk, by use of the processed binding quantity data Dw1 to Dw3840 having been acquired by the processed binding quantity acquiring section 86. Also, the hit compound extracting section 88 makes a comparison between each of the values of the processed binding quantity data Dw1 to Dw3840 and the threshold value Qw having been set by the threshold value setting section 87. In accordance with the results of the comparison, the hit compound extracting section 88 extracts the protein Ta, which corresponds to the processed binding quantity data Dw having a value larger than the threshold value Qw, as the hit compound (in this case, the hit protein) Hk. The thus extracted hit compound Hk is displayed on the display device 50.

In the embodiments described above, the gold film Me is formed on the total reflection surface Ls. Alternatively, a metal film, which is constituted of a metal other than gold, may be formed on the total reflection surface Ls.

The screening method in accordance with the present invention is also applicable to, for example, screening operations, which are performed by use of a leaky mode analysis apparatus, and screening operations, which are performed by use of an apparatus utilizing one of the other analysis principles.

As an example of an analysis method for performing the measurement of the refractive index alteration quantity, which analysis method is other than the analysis method utilizing the attenuated total reflection, there may be mentioned an interference technique.

What is claimed is:

1. A screening method, in which binding quantity data each representing a quantity of binding of a single kind of a ligand to each of multiple kinds of analytes are acquired from measurement of a refractive index alteration quantity at an interface of an actual measurement region or a reference measurement region on a base body block, and in which an analyte having binding affinity to the ligand is identified from the multiple kinds of analytes and in accordance with the binding quantity data, the method comprising the steps of:

i) performing an operation for bringing individual analyte solutions, each containing one of the multiple kinds of analytes, into contact with the actual measurement region, to which the ligand has been fixed, wherein multiple operations are performed corresponding to each of the analyte solutions, which each contain one of the multiple kinds of analytes, ii) acquiring values of actual measurement data from the multiple operations in i), wherein each value of actual measurement data represents a refractive index alteration quantity obtained from the corresponding operation, iii) performing an operation for bringing the analyte solution into contact with the reference measurement region, to which no ligand has been fixed, wherein multiple operations are performed corresponding to each of the analyte solutions, which each contain one of the multiple kinds of analytes, iv) acquiring values of reference measurement data from the multiple operations in iii), wherein each value of reference measurement data represents a refractive index alteration quantity and corresponds to the actual measurement data obtained from ii) using a same analyte, v) subtracting the values of the reference measurement data from the corresponding values of the actual measurement data, unprocessed binding quantity data being thereby acquired, vi) calculating a relationship between the values of the reference measurement data and the values of the unprocessed binding quantity data, which vary in accordance with the values of the reference measurement data, wherein the values of the reference measurement data and the values of the unprocessed binding quantity data are of analytes unbound to the ligand, vii) making calculation in accordance with the thus calculated relationship to find variation components, each of which is contained in one of the unprocessed binding quantity data and corresponds to one of the reference measurement data of all analytes unbound and bound to the ligand, viii) subtracting each of the values of the variation components, each of which is contained in one of the unprocessed binding quantity data, from the corresponding one of the values of the unprocessed binding quantity data, processed binding quantity data being thereby acquired, and ix) utilizing the thus acquired processed binding quantity data as the binding quantity data for use in identifying the analyte having binding affinity to the ligand.

2. A screening method, in which binding quantity data each representing a quantity of binding of a single kind of an analyte and each of multiple kinds of ligands are acquired from measurement of a refractive index alteration quantity at an interface of an actual measurement region or a reference measurement region on a base body block, and in which a ligand having binding affinity to the analyte is identified from the multiple kinds of ligands and in accordance with the binding quantity data, the method comprising the steps of:

i) performing an operation for bringing an analyte solution, which contains the single kind of the analyte, into contact with the actual measurement region, having fixed thereon one of the multiple kinds of the ligands, wherein multiple operations are performed corresponding to each of the ligands, ii) acquiring values of actual measurement data from the multiple operations in i), wherein each value of actual measurement data represents a refractive index alteration quantity obtained from the corresponding operation, iii) performing an operation for bringing the analyte solution into contact with the reference measurement region, wherein multiple operations are performed corresponding to each of the ligands, iv) acquiring values of reference measurement data from the multiple operations in iii), wherein each value of reference measurement data represents a refractive index alteration quantity and corresponds to the actual measurement data obtained from ii) using a same analyte, v) subtracting the values of the reference measurement data from the corresponding values of the actual measurement data, unprocessed binding quantity data being thereby acquired, vi) calculating a relationship between the values of the reference measurement data and the values of the unprocessed binding quantity data, which vary in accordance with the values of the reference measurement data, wherein the values of the reference measurement data and the values of the unprocessed binding quantity data are of analytes having not undergone binding with the ligand, vii) making calculation in accordance with the thus calculated relationship to find variation components, each of which is contained in one of the unprocessed binding quantity data and corresponds to one of the reference measurement data of all analytes unbound and bound to the ligand, viii) subtracting each of the values of the variation components, each of which is contained in one of the unprocessed binding quantity data, from the corresponding one of the values of the unprocessed binding quantity data, processed binding quantity data being thereby acquired, and ix) utilizing the thus acquired processed binding quantity data as the binding quantity data for use in identifying ligand having binding affinity to the analyte.

3. A screening method as defined in claim 1 wherein the variation components are calculated with a function which approximately represents the relationship between the values of the reference measurement data and the values of the unprocessed binding quantity data.

4. A screening method as defined in claim 2 wherein the variation components are calculated with a function which approximately represents the relationship between the values of the reference measurement data and the values of the unprocessed binding quantity data.

5. A screening method as defined in claim 1 wherein the refractive index alteration quantity occurs due to surface plasmon resonance.

6. A screening method as defined in claim 2 wherein the refractive index alteration quantity occurs due to surface plasmon resonance.

7. A screening method as defined in claim 3 wherein the refractive index alteration quantity occurs due to surface plasmon resonance.

8. A screening method as defined in claim 4 wherein the refractive index alteration quantity occurs due to surface plasmon resonance.

9. A screening apparatus, comprising:

i) an analysis section for acquiring binding quantity data, each of which represents a quantity of binding of a single kind of a ligand and each of multiple kinds of analytes acquired from measurement of a refractive index alteration quantity at an interface of an actual measurement region or a reference measurement region on a base body block, and ii) a screening section for identifying an analyte, having binding affinity to the ligand, from the multiple kinds of analytes and in accordance with the binding quantity data, the analysis section being constituted for:

a) performing an operation for bringing individual analyte solutions, each containing one of the multiple kinds of analytes, into contact with the actual measurement region, to which the single kind of the ligand has been fixed, wherein multiple operations are performed corresponding to each of the analyte solutions, which each contain one of the multiple kinds of analytes, b) acquiring values of actual measurement data from the multiple operations in a), wherein each value of actual measurement data represents a refractive index alteration quantity obtained from the corresponding operation, c) performing an operation for bringing the analyte solution into contact with the reference measurement region, to which no ligand has been fixed, wherein multiple operations are performed corresponding to each of the analyte solutions, which each contain one of the multiple kinds of analytes, and d) acquiring values of reference measurement data from the multiple operations in c), wherein each value of reference measurement data represents a refractive index alteration quantity and corresponds to the actual measurement data obtained from b) using a same analyte, and the screening section being provided with:

a) a storage section for storing information representing the values of the actual measurement data and the values of the reference measurement data, which have been acquired by the analysis section, b) a pre-processing section for subtracting each of the values of the reference measurement data from the corresponding one of the values of the actual measurement data, and thereby acquiring unprocessed binding quantity data, c) a variation relationship acquiring section for calculating a relationship between the values of the reference measurement data and the values of the unprocessed binding quantity data, which vary in accordance with the values of the reference measurement data, wherein the values of the reference measurement data and the values of the unprocessed binding quantity data are of analytes unbound to the ligand, d) a variation component acquiring section for making calculation in accordance with the thus calculated relationship to find each of variation components, each of which is contained in one of the unprocessed binding quantity data and corresponds to one of the reference measurement data of all analytes unbound and bound to the ligand, and e) a processed binding quantity acquiring section for subtracting each of the values of the variation components, each of which is contained in one of the unprocessed binding quantity data, from the corresponding one of the values of the unprocessed binding quantity data, and thereby acquiring processed binding quantity data, the thus acquired processed binding quantity data being utilized as the binding quantity data for use in extracting the analyte, which is capable of undergoing the binding with the ligand.

10. A screening apparatus, comprising:

i) an analysis section for acquiring binding quantity data, each of which represents a quantity of binding of a single kind of an analyte and each of multiple kinds of ligands acquired from measurement of a refractive index alteration quantity at an interface of an actual measurement region or a reference measurement region on a base body block, and ii) a screening section for identifying a ligand, having binding affinity to the analyte, from the multiple kinds of ligands and in accordance with the binding quantity data, the analysis section being constituted for:

a) performing an operation for bringing an analyte solution, which contains the single kind of the analyte, into contact with the actual measurement region, having fixed thereon one of the multiple kinds of the ligands, wherein multiple operations are performed corresponding to each of the ligands, b) acquiring values of actual measurement data from the multiple operations in a), wherein each value of actual measurement data represents a refractive index alteration quantity obtained from the corresponding operation, c) performing an operation for bringing the analyte solution into contact with the reference measurement region, wherein multiple operations are performed corresponding to each of the ligands, and d) acquiring values of reference measurement data from the multiple operations in c), wherein each value of reference measurement data represents a refractive index alteration quantity and corresponds to the actual measurement data obtained from b) using a same analyte, and the screening section being provided with:

a) a storage section for storing information representing the values of the actual measurement data and the values of the reference measurement data, which have been acquired by the analysis section, b) a pre-processing section for subtracting each of the values of the reference measurement data from the corresponding one of the values of the actual measurement data, and thereby acquiring unprocessed binding quantity data, c) a variation relationship acquiring section for calculating a relationship between the values of the reference measurement data and the values of the unprocessed binding quantity data, which vary in accordance with the values of the reference measurement data, wherein the values of the reference measurement data and the values of the unprocessed binding quantity data are of analytes unbound to the ligand, d) a variation component acquiring section for making calculation in accordance with the thus calculated relationship to find each of variation components, each of which is contained in one of the unprocessed binding quantity data and corresponds to one of the reference measurement data of all analytes unbound and bound to the ligand, and e) a processed binding quantity acquiring section for subtracting each of the values of the variation components, each of which is contained in one of the unprocessed binding quantity data, from the corresponding one of the values of the unprocessed binding quantity data, and thereby acquiring processed binding quantity data, the thus acquired processed binding quantity data being utilized as the binding quantity data for use in extracting the ligand, which is capable of undergoing the binding with the analyte.

* * * * *